US007250492B2

(12) United States Patent
Chen

(10) Patent No.: US 7,250,492 B2
(45) Date of Patent: Jul. 31, 2007

(54) COMPOSITIONS AND METHODS FOR INHIBITION OF CANCER INVASION AND ANGIOGENESIS

(75) Inventor: Wen-Tien Chen, Stony Brook, NY (US)

(73) Assignee: The Research Foundation at State University of New York, Stony Brook, NY (US)

( * ) Notice: Subject to any disclaimer, the term of this patent is extended or adjusted under 35 U.S.C. 154(b) by 456 days.

(21) Appl. No.: 10/727,211

(22) Filed: Dec. 3, 2003

(65) Prior Publication Data

US 2004/0115202 A1 Jun. 17, 2004

Related U.S. Application Data

(63) Continuation of application No. 09/823,277, filed on Mar. 30, 2001, now abandoned, which is a continuation-in-part of application No. 09/541,785, filed on Apr. 3, 2000, now Pat. No. 6,573,096.

(60) Provisional application No. 60/193,987, filed on Apr. 1, 2000.

(51) Int. Cl.
C12P 21/08 (2006.01)
(52) U.S. Cl. ............... 530/387.3; 530/388.2; 435/332
(58) Field of Classification Search ............ 530/387.3, 530/387.7, 388.26, 388.8, 350, 388.2; 435/332
See application file for complete search history.

(56) References Cited

U.S. PATENT DOCUMENTS

| 5,092,885 A | 3/1992 | Yamada et al. |
| 5,221,622 A | 6/1993 | Chen |
| 5,545,405 A | 8/1996 | Page |
| 5,753,230 A | 5/1998 | Brooks et al. |
| 5,942,385 A | 8/1999 | Hirth |
| 5,980,896 A | 11/1999 | Hellstrom et al. |
| 6,123,941 A | 9/2000 | Bissell et al. |
| 6,193,968 B1 | 2/2001 | Carron et al. |
| 6,258,597 B1 | 7/2001 | Bachovchin et al. |
| 2003/0138432 A1* | 7/2003 | Glazier ............ 424/178.1 |

FOREIGN PATENT DOCUMENTS

WO        WO96/38550        12/1996

OTHER PUBLICATIONS

Abbott et al. (Eur. J. Biochem. 1999; 266: 798-810).*
Greenspan et al. (Nature Biotechnology. 1999; 7: 936-937).*
George et al. (Circulation. 1998; 97: 900-906).*
Stancoviski et al. (Proceedings of the National Academy of Science USA. 1991; 88: 8691-8695).*
Jiang et al. (J. Biol. Chem. Feb. 11, 2005; 280 (6): 4656-4662).*
Dong, R.P., et al., "Correlation of the epitopes defined by anti-CD26 mAbs and CD26 function", *Molecular Immunology* 1998, 35(1):13-21.
Ghersi, G., et al., "Regulation of fibroblast migration on collagenous matrix by a cell surface peptidase complex", *Journal of Biological Chemistry* 2002, 277(32):29231-29241.
Loster, K., et al., "The cysteine-rich region of dipeptidyl peptidase IV (CD 26) is the collagen-binding site", *Biochemical and Biophysical Research Communications* 1995, 217(1):341-348.
Zukowska-Grojec, Z., et al., "Neuropeptide Y.A novel angiogenic factor from the sympathetic nerves and endothelium", *Circulation Research* 1998, 83(2):187-195.
J. Heins, P. Welker, Chr. Schönlein, I. Born, B. Hartrodt, K. Neubert, D. Tsuru and A. Barth, "Mechanism of proline-specific proteinases: (I) substrate specificity of dipeptidyl peptidase IV from pig kidney and proline-specific endopeptidase from *Flavobacterium meningosepticum*," *Biochimica et Biophysica Acta* (1988) 954:161-169.
Wen-Tien Chen and Jaw-Yuan Wang, "Specialized Surface Protrusions of Invasive Cells, Invadopodia and Lamellipodia, Have Differential MT1-MMP, MMP-2, and TIMP-2 Localization," *Annals of the New York Acad. Of Sciences* (1999) 878: 361-371.
Susette C. Mueller, Giulio Ghersi, Steven K. Akiyama, Qing-Xiang Amy Sang, Linda Howard, Mayra Pineiro-Sanchez, Hirokazu Nakahara, Yunyun Yeh, and Wen-Tien Chen, "A Novel Protease-docking Function of Integrin at Invadopodia", *The Journal of Biological Chemistry* (1999) 274/35: 24947-24952.
Donald Ingber and Judah Folkman, "Inhibition of Angiogenesis Through Modulation of Collagen Metabolism," *Laboratory Investigation*. (1988) 59/1:. 44-51.
Marsha A. Moses, Judith Sudhalter, Robert Langer, "Identification of an Inhibitor of Neovascularization from Cartilage," *Science* 1990, 248: 1408-1410.

(Continued)

Primary Examiner—Stephen L. Rawlings
(74) Attorney, Agent, or Firm—Hoffmann & Baron, LLP

(57) ABSTRACT

The invention provides antibodies that specifically bind a membrane protease complex, the complex consisting of two homodimers of seprase and dipeptidyl peptidase IV (DPPIV), obtained from mammalian, preferably human cell membranes. The antibodies specifically bind the DPPIV protease of the seprase-DPPIV complex. This membrane protease complex resides on cell surface invadopodia at the leading edge of angiogenic endothelia, migratory fibroblasts, and invading cancer cells. The antibodies and immunoconjugates of the invention specifically bind the membrane protease complex at the cell surface invadopodia, yet fail to react with resting cells in adjacent human tissues and blood vessels. These antibodies and immunoconjugates block interaction of collagen matrix with the seprase-DPPIV complex in the invasive cells during angiogenesis and cancer spreading but not that with other endothelia or tumor cells. The invention further provides methods for identifying and of using DPPIV antagonists to inhibit capillary sprouting, angiogenesis and cancer invasion in tumor tissues and metastases. Also provided are therapeutic compositions comprising DPPIV antagonists.

3 Claims, 22 Drawing Sheets

OTHER PUBLICATIONS

Christine H. Blood and Bruce R. Zetter, "Tumor interactions with the vasculature: angiogenesis and tumor metastasis," *Biochimica et Biophysica Acta* (1990) 1032: 89-118.

Leslie A. Goldstein and Wen-Tien Chen, "Identification of an Alternatively Spliced Seprase mRNA That Encodes a Novel Intracellular Isoform," *The Journal of Biological Chemistry* (2000) 275/4: 2554-2559.

Wanda Auerbach and Robert Auerbach, "Angiogenesis Inhibition: A Review," *Pharmac. Ther.* (1994) 63: 265-311.

Rakesh K. Jain, "Vascular and interstitial barriers to delivery of therapeutic agents in tumors," *Cancer and Metastasis Reviews* (1990) 9: 253-266.

Sally S. Seaver, Ph.D., "Monoclonal Antibodies in Industry: More Difficult Than Originally Thought," *Genetic Engineering News* (1994) 14/14: 10 and 21.

William J. Harris and Steven Emery, "Therpeutic antibodies—the coming of age," *Trends in Biotechnology* (1993) 11: 42-44.

Trisha Gura "Systems for Identifying New Drugs Are Often Faulty," *Science*(1997) 278: 1041-1042.

Eryl Liddell and Ian Weeks "Antibody Technology" *Bios Scientific Publishers* (1995) 23-44.

Sabine Hartel-Schenk, Nikolaus Loch, Martin Zimmermann and Werner Reutter, "Development of monoclonal antibodies against different protein and carbohydrate epitopes of dipeptidyl peptidase IV from rat liver plasma membranes," *Eur. J. Biochem* (1991) 196: 349-355.

Dirk Reinhold, Ute Bank, Frank Bühling, Klaus Neubert, Taila Mattern, Artur Jochen Ulmer, Hans-Dieter Flad, and Siegfried Ansorge, "Dipeptidyl Peptidase IV (CD26) on Human Lymphocytes. Synthetic Inhibitors of and Antibodies against Dipeptidyl Peptidase IV Suppress the Proliferation of Pokeweed Mitogen-Stimulated Peripheral Blood Mononuclear Cells, and IL-2 and IL-6 Production," *Immunobiology* (1993) 188: 403-414.

J.J. Van Den Oord, "Expression of CD26/dipeptidyl-peptidase IV in benign and malignant pigment-cell lesions of the skin," *British Journal of Dermatology* (1998) 138: 615-621.

Hung-Chi Cheng, Mossaad Abdel-Ghany, Randolph C. Elble, and Bendicht U. Pauli, "Lung Endothelial Dipeptidyl Peptidase IV Promotes Adhesion and Metastasis of Rat Breast Cancer Cells via Tumor Cell Surface-associated Fibronectin," *The Journal of Biological Chemistry* (1998) 273/37: 24207-24215.

T. Mattern, A. C. Feller, B. Kniep, H. -D. Flad, and A. J. Ulmer, "Comparative studies on three monoclonal antibodies (anti DPPIV, anti Ta1, IOT15) recognizing antigens clustered in Cdw26," *Immunobiology* (1988) 178(1/2): 110, Abstract H.12.

Arao, Shuichi, et al., "$\beta 1$ Integrins Play an Essential Role in Adhesion and Invasion of Pancreatic Carcinoma Cells", *Pancreas* 2000, 20(2):129-137.

Barbet, Jacques, et al., "Pretargeting with the Affinity Enhancement System for Radioimmunotherapy", *Cancer Biotherapy & Radiopharmaceuticals* 1999, 14(3):153-166.

Duke-Cohan, Jonathan, et al., "Targeting of an Activated T-Cell Subset Using a Bispecific Antibody-Toxin Conjugate Directed Against CD4 and CD26", *Blood* 1993, 82(7):2224-2234.

Elble, R.C., et al., "Lu-ECAM-1 and DPP IV in Lung Metastasis", *Curr. Top Microbiol Immunol* 1996, 213(1):107-122.

Fukushima, Yuji, et al., "Integrin $\alpha 3\beta 1$-Mediated Interaction with Laminin-5 Stimulates Adhesion, Migration and Invasion of Malignant Glioma Cells", *Int. J. Cancer* 1998, 76:63-72.

Abdel-Ghany, Mossaad, et al., "Truncated Dipeptidyl Peptidase IV is a Potent Anti-Adhesion and Anti-Metastasis Peptide for Rat Breast Cancer Cells", *Invasion Metastatis* 1998, 18:35-43.

Ghersi, Guilio, et al., "Critical role of dipeptidyl peptidase IV in neuropeptide Y-mediated endothelial cell migration in response to wounding", *Peptides* 2001, 22:453-458.

Johnson, Robert C., et al., "Lung Endothelial Dipeptidyl IV is an Adhesion Molecule for Lung-metastatic Rat Breast and Prostate Carcinoma Cells", *The Journal of Cell Biology* 1993, 121(6):1423-1432.

Klominek, Julius, et al., "Differential Motile Response of Human Malignant Mesothelioma Cells to Fibronectin, Laminin and Collagen Type IV: The Role of $\beta_1$ Integrins", *Int. J. Cancer* 1997, 72:1034-1044.

Kotani, T., et al., "Diagnostic Usefulness of Dipeptidyl Aminopeptidase IV Monoclonal Antibody in Paraffin-Embedded Thyroid Follicular Tumours", *Journal of Pathology* 1992, 168:41-45.

Lundstrom, Ase, et al., "The Role of $\alpha 2\beta 1$ and $\alpha 3\beta 1$ Integrin Receptors in the Initial Anchoring of MDA-MB-231 Human Breast Cancer Cells to Cortical Bone Matrix", *Biochemical and Biophysical Research Communications* 1998, 250:735-740.

Masumoto, Akihide, et al., "Role of $\beta 1$ Integrins in Adhesion and Invasion of Hepatocellular Carcinoma Cells", *Hepatology* 1999, 29(1):68-74.

Schroder, Soren, et al., "Carcinoembryonic Antigen and Nonspecific Cross-Reacting Antigen in Thyroid Cancer", *The American Journal of Surgical Pathology* 1987, 11(2):100-108.

\* cited by examiner

FAP1 + 2    FAP11 + 4    GPDH

DPPF1 + DPPR2

ANTI-SEPRASE

ANTI-DPPIV

SEQUENCE LISTING

```
<160> NUMBER OF SEQ ID NOS: 4

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (2)..(4)
<223> OTHER INFORMATION: X is any amino acid

<400> SEQUENCE: 1

Gly Xaa Ser Xaa Gly
1               5

<210> SEQ ID NO 2
<211> LENGTH: 5
<212> TYPE: PRT
<213> ORGANISM: Homo sapiens

<400> SEQUENCE: 2

Gly Trp Ser Tyr Gly
1               5

<210> SEQ ID NO 3
<211> LENGTH: 27
<212> TYPE: DNA
<213> ORGANISM: Homo sapiens

<400> SEQUENCE: 3
aggcactgaa ctgatgagtc cgtgagg                                    27

<210> SEQ ID NO 4
<211> LENGTH: 25
<212> TYPE: DNA
<213> ORGANISM: Homo sapiens
```

-continued

```
<400> SEQUENCE: 4
tgaagaggaa gtttcgtcct cacgg                                  25
```

COMPOSITIONS AND METHODS FOR INHIBITION OF CANCER INVASION AND ANGIOGENESIS

RELATED APPLICATIONS

This application is a continuation of U.S. application Ser. No. 09/823,277 filed on Mar. 30, 2001, now abandoned which is a continuation-in-part of U.S. application Ser. No. 09/541,785 filed on Apr. 3, 2000, now U.S. Pat. No. 6,573,096, which claims the benefit of U.S. Provisional Application No. 60/193,987 filed on Apr. 1, 2000. The specifications of U.S. application Ser. No. 09/823,277, U.S. application Ser. No. 09/541,785, and U.S. Provisional Application No. 60/193,987 are hereby incorporated by reference in their entirety.

This work was supported by grants from one or more of the following: U.S. Public Health Service, National Cancer Institute and The National Institute of Aging. The government may have certain rights to this invention.

FIELD OF THE INVENTION

The present invention relates generally to the field of medicine, and relates specifically to angiogenesis and metastasis of cancer tissues, as well as treatment of cardiovascular disease. Specifically the invention relates to the use of modulators, including antagonists and agonists of the serine integral membrane protease, dipeptidyl peptidase IV (DPPIV also known as CD26).

BACKGROUND OF THE INVENTION

Growth of new blood vessels (angiogenesis) plays a key role in tissue repair and in cancer progression. The invasion of cells into a connective tissue barrier during angiogenesis requires remodeling of the extracellular matrix (ECM) by migratory cells (Martin, 1997). In cancer invasion such cellular activities occur on membrane protrusions invadopodia (Chen, 1979) which exhibit dynamic membrane mobility, ECM adhesion and degradation. Thus, cellular invasion is an important process for cancer metastasis (Stetler-Stevenson et al., 1993). Several classes of proteases including matrix metalloproteinases (MMPs), serine proteases, cysteine proteases (cathepsin B and cathepsin L), and aspartic acid proteases (cathepsin D) can degrade proteins in the ECM (Chen, 1992). And invading cancer cells possess ECM degrading proteolytic enzymes that are concentrated at specialized plasma membrane protrusions, termed invadopodia (Chen et al., 1994). Recent studies showed that integral membrane proteases might contribute significantly to ECM degradation and ultimately cancer invasion by virtue of their location at invadopodia (Monsky and Chen, 1993).

Recent evidence has demonstrated the involvement of serine-integral membrane proteases (SIMP), including dipeptidyl peptidase IV (DPPIV)/CD26 and seprase, in cell surface proteolysis (Chen, 1996). SIMP members are type II transmembrane proteins, with cytoplasmic tails that contain 6 amino acids (a.a.) followed by a transmembrane domain of 20 a.a. (in the case of seprase) or 22 a.a. (in the case of DPPIV) at the N-terminus and a stretch of 200 a.a. at the C-terminus that constitutes a catalytic region with the catalytic serine in a non-classical orientation (Goldstein et al., 1997; Pineiro-Sanchez et al., 1997).

DPPIV specifically removes N-terminal dipeptides from oligo-peptides, which include Neuro-Peptide Y and other peptide hormones, with either L-proline, L-hydroxyproline, or L-alanine at the penultimate position (Heins et al., 1988, Walter et al., 1980). DPPIV has been shown to be an adhesion receptor for collagen (Bauvois, 1988; Hanski et al., 1988; Loster et al., 1995) or fibronectin (Cheng et al., 1998; Johnson, et al., 1993; Piazza et al., 1989). In addition, a recent report showed that DPPIV also possesses a seprase-like gelatinase activity and therefore endopeptidase activity (Bermpohl et al., 1998), suggesting its involvement in collagen degradation. DPPIV is expressed constitutively on brush border membranes of intestine and kidney epithelial cells (Yaron and Naider, 1993; Morimoto and Schlossman, 1994).

Seprase, originally identified as a 170 kDa membrane-bound gelatinase is expressed on invadopodia of highly aggressive melanoma LOX cells (Aoyama and Chen, 1990; Mueller et al., 1999; Monsky et al., 1994). The active enzyme is a homodimer of 97 kDa subunits, which are proteolytically inactive (Pineiro-Sanchez et al., 1997). Analysis of the deduced amino acid sequence from a cDNA that encodes the 97 kDa subunit (Goldstein et al., 1997) revealed that it is homologous to DPPIV, and is essentially identical to fibroblast activation protein α (FAPα) (Scanlan et al., 1994), which is expressed on reactive stromal fibroblasts of epithelial cancers and healing wounds (Garin-Chesa et al., 1990). In addition, DNA and protein analysis of embryonic tissues has suggested potential additional members of SIMP (Bermpohl et al., 1998).

A growing body of evidence indicates that angiogenesis is essential to the progression of cancer. Angiogenesis is the sprouting of new capillaries from preexisting blood vessels. Normally, angiogenesis in mammals is confined to the reproductive system, embryogenesis and development, and repair after injury. However, angiogenesis can also occur in pathological conditions such as cancer, retinal neovascularization, neovascularization in atherosclerotic plaques, hemangiomas, artritis, and psoriasis. See Folkman, 1995. Without vascularization, tumors may remain for years as small (less than a few millimeters) asymptomatic lesions. Weidner et al. (1991). Angiogenesis allows the cancer cells access to the circulatory system. The new blood vessels also provide a gateway for cancer cells to enter the circulation and metastasize to distant sites (Folkmnan 1990; Klagsbrunn and Soker, 1993).

As in cancer cell invasion, angiogenesis involves matrix degradation by migrating endothelial cells at the invasion front; proteases including matrix metalloproteases (MMPs) (Hiraoka et al., 1998; Brooks et al., 1998) and plasminogen activators (Pepper et al., 1993) are essential. However, novel membrane-bound proteases active at sites of angiogenesis have not yet been identified.

Several approaches for inhibition of angiogenesis have been proposed as useful therapies for restricting tumor growth. These include inhibition of angiogenesis by (1) inhibition of release of "angiogenic molecules" such as VEGF (Vascular endothelial growth factor) and basic.FGF (fibroblast growth factor), (2) neutralization of angiogenic molecules, such as by use of anti-b.FGF antibodies, (3) inhibition targeted to alpha$_v$.beta$_3$ integrin, and (4) inhibition of the endothelial cell response to angiogenic stimuli. This latter strategy has received particular attention, and Folkman et al., Cancer Biology, 3:89–96 (1992), have described several endothelial cell response inhibitors, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin D₃ analogs, alpha-interferon, and the like that might be used to inhibit angiogenesis.

Monoclonal antibodies (MAbs) to human tumor-associated differentiation antigens offer promise for the "targeting" of various antitumor agents such as radioisotopes, chemotherapeutic drugs, and toxins. [Order, in. "Monoclonal Antibodies for Cancer Detection and Therapy", Baldwin and Byers, (eds.), London, Academic Press (1985)]. In addition, some monoclonal antibodies have the advantage of killing tumor cells via antibody-dependent cellular cytotoxicity (ADCC) or complement-dependent cytotoxicity (CDC) in the presence of human effector cells or serum [Hellstrom et al., Proc. Natl. Acad. Sci. USA 83:7059–7063 (1986)], and there are a few monoclonal antibodies that have a direct antitumor activity which does not depend on any host component [Drebin et al., Oncogene 2:387–394 (1988)].

For additional proposed inhibitors of angiogenesis, see Blood et al., Bioch. Biophys. Acta., 1032:89–118 (1990) for a general review of angiogenesis and tumor metastasis; also Moses et al., Science, 248:1408–1410 (1990) describes a protein inhibitor of angiogenesis derived from cartilage; and Ingber & Folkman, Lab. Invest. 59:44–51 (1988) describes inhibition of angiogenesis through modulation of collagen metabolism.

U.S. Pat. No. 5,092,885, of Yamada et al. discloses laminin peptides with angiogenesis-blocking activity. U.S. Pat. No. 5,112,946 of Maione et al. discloses modified PF4 compositions as inhibitors of angiogenesis. U.S. Pat. No. 5,192,744, discloses human thrombospondin for use as an inhibitor of angiogenesis. U.S. Pat. No. 5,202,352 discloses intravascular embolizing agents containing angiogenesis inhibiting substances in oils, emulsions or suspensions. U.S. Pat. No. 5,766,591 discloses antagonists of vitronectin $\alpha_v \cdot \beta_3$ as angiogenesis inhibitors.

U.S. Pat. No. 5,980,896 of Hellstrom et al. discloses antibodies and immunoconjugates reactive with human carcinomas and is especially useful in practicing the full scope of the present invention. Among the disclosed compositions and methods which are especially applicable to the present invention are: chimeric antibodies, immunoconjugates thereof and their methods of preparation and use; and anti-tumor drugs, cytotoxins, radioactive agents and enzymes useful in immunoconjugate compositions. The specification of U.S. Pat. No. 5,980,896 is hereby incorporated by reference in its entirety.

There is still a need, however for novel and more effective angiogenesis modulation therapies for use alone or in combination with one or more of the currently available therapies for treatment of growth and proliferative disorders involving angiogenesis.

SUMMARY OF THE INVENTION

The invention provides monospecific antibodies that specifically bind an epitope of a mammalian DPPIV (dipeptidyl peptidase IV/CD26), such as a human DPPIV. Preferably, the monospecific antibodies inhibit angiogenesis and tumor invasiveness.

Also provided are bispecific antibodies with binding specificity for two epitopes, one being an epitope of DPPIV. Bispecific antibodies of the present invention include those in which the second epitope bound is an epitope of seprase, MT1-MMP, MMP-2 or $\alpha(3)\beta(1)$-integrin.

The present invention further provides immunoconjugates comprising a monospecific or a bispecific antibody which specifically binds an epitope of human DPPIV and inhibits angiogenesis, the antibody being joined to a therapeutic agent.

In yet another aspect the invention provides pharmaceutical compositions for inhibiting angiogenesis comprising an effective amount of an antibody which specifically binds an epitope of a mammalian DPPIV and inhibits angiogenesis, the antibody being formulated in a pharmaceutically acceptable carrier.

In yet another aspect the invention provides pharmaceutical compositions for inhibiting angiogenesis comprising an effective amount of an immunoconjugate of an antibody which specifically binds an epitope of a mammalian DPPIV and inhibits angiogenesis, the antibody being formulated in a pharmaceutically acceptable carrier.

The present invention yet further provides a method of treating a mammal suffering from a growth or proliferative disorder associated with angiogenesis, comprising administering to the site of angiogenesis an effective amount of an antibody which specifically binds an epitope of a human DPPIV and inhibits angiogenesis.

In yet another aspect the present invention provides a method of treating a mammal suffering from a growth or proliferative disorder involving angiogenesis, comprising administering to the site of angiogenesis an effective amount of an immunoconjugate which specifically binds an epitope of a human DPPIV and inhibits angiogenesis.

In a further aspect the present invention provides continuous cell lines which produce monospecific antibodies that specifically bind an epitope of a mammalian DPPIV and thereby inhibit angiogenesis.

In a yet further aspect the present invention provides a method of stimulating angiogenesis in a mammal suffering from disease or disorder that may be remedied by an increased blood supply, such as for instance cardiovascular disease, by administering an angiogenesis-stimulating amount of a DPPIV stimulator, whereby the blood supply to the affected tissue is increased.

DETAILED DESCRIPTION OF THE INVENTION

Figure 1:
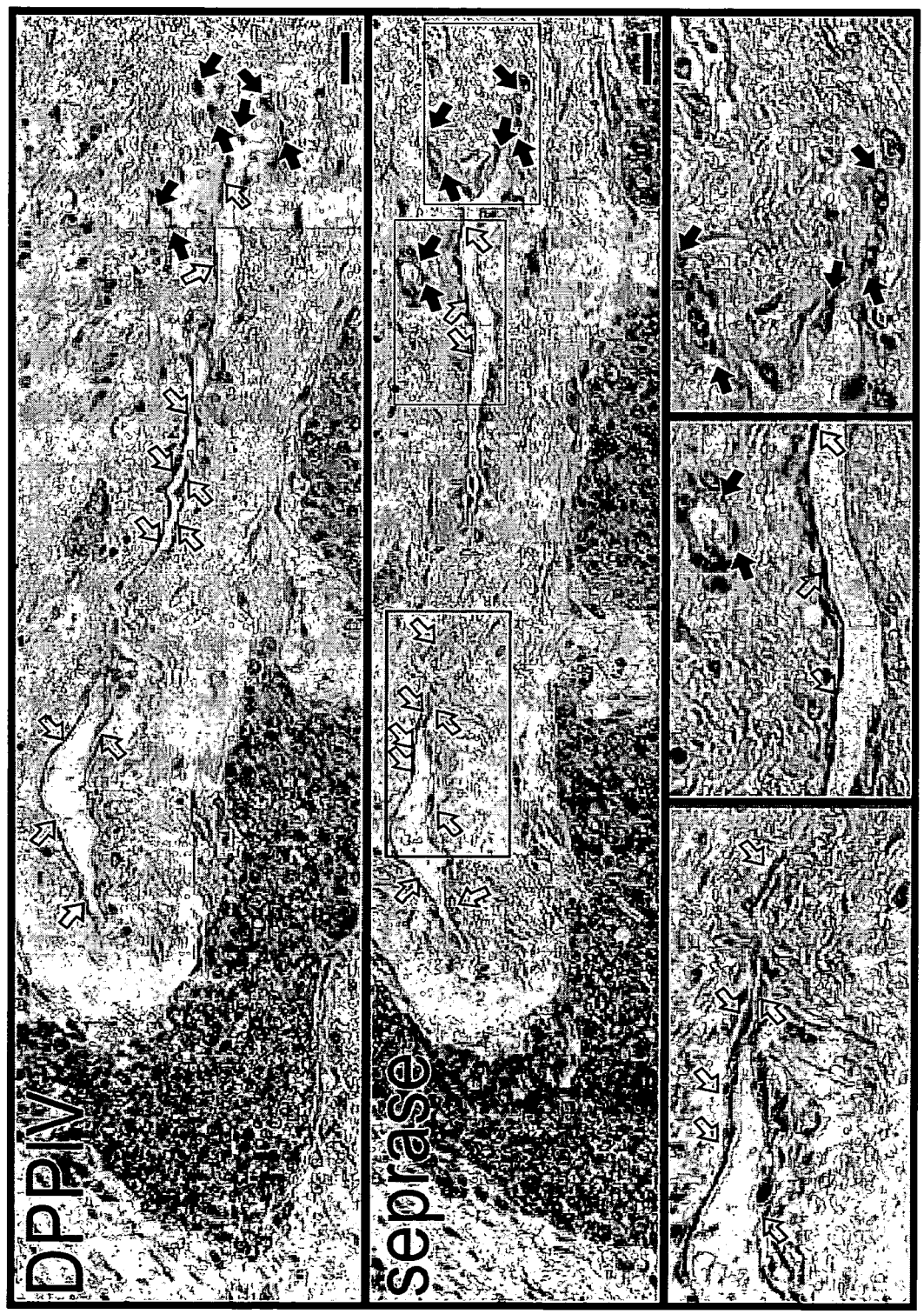
FIG. 1. Seprase and DPPIV expression in the endothelial cells of sprouting vessels but not in differentiated vessels in human malignant breast carcinoma. Both seprase (middle panel) and DPPIV (upper panel) are present in the endothelial cells of sprouting microvessels (brown stains indicated by black solid arrows) but not in endothelia of adjacent vessels (open arrows). Adjacent to microvessels are cell clusters of invasive breast carcinoma that stain positively for seprase and DPPIV. The bottom panel is an expanded view of seprase staining of vessels. Paraffin sections of breast carcinoma tissue were stained with the anti-seprase mAb D28 or the anti-DPPIV mAb E26. Bar=100 µm.

Definitions: As used herein, the following words or phrases have the specified meanings.

As used herein, "fragment" is defined as at least a portion of the variable region of the immunoglobulin molecule which binds to its target, i.e. the antigen binding region. Some of the constant region of the immunoglobulin may be included.

As used herein, an "immunoconjugate" means any molecule or ligand such as an antibody or growth factor chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as it is able to bind its target. Examples of immunoconjugates include immunotoxins and antibody conjugates.

As used herein, "selectively killing" means killing those cells to which the antibody binds. As used herein, examples of "carcinomas" include, but are not limited to the following: bladder, breast, colon, liver, lung, ovarian, and pancreatic carcinomas. As used herein, "immunotoxin" means an antibody or growth factor chemically or biologically linked to a cytotoxin or cytotoxic agent.

As used herein, an "effective amount" is an amount of the antibody, immunoconjugate, recombinant molecule which kills cells or inhibits the proliferation thereof. As used herein, "competitively inhibits" means being capable of binding to the same target as another molecule. With regard to an antibody, competitively inhibits mean that the antibody is capable of recognizing and binding the same antigen binding region to which another antibody is directed.

As used herein, "antigen-binding region" means that part of the antibody, recombinant molecule, the fusion protein, or the immunoconjugate of the invention which recognizes the target or portions thereof. As used herein, "therapeutic agent" means any agent useful for therapy including anti-tumor drugs, cytotoxins, cytotoxin agents, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents. As used herein, "a cytotoxin or cytotoxic agent" means any agent that is detrimental to cells. Examples include Taxol® (paclitaxel), cytochalasin B, gramicidin D, ethidium bromide, emetine, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, a chemotherapeutic regimen refers to any treatment with a chemotherapeutic agent. Examples of chemotherapeutic agents include, for example, the anti-tumor drugs listed above.

As used herein, "a radioactive agent" includes any radioisotope which is effective in destroying a tumor. Examples include, but are not limited to, cobalt-60 and X-ray emitters. Additionally, naturally occurring radioactive elements such as uranium, radium, and thorium which typically represent mixtures of radioisotopes, are suitable examples of a radioactive agent.

As used herein, "administering" means oral administration, administration as a suppository, topical contact, intravenous, intraperitoneal, intramuscular or subcutaneous administration, or the implantation of a slow-release device such as a miniosmotic pump, to the subject. As used herein, "curing" means to provide substantially complete tumor regression so that the tumor is not palpable.

As used herein, "tumor associated antigens" means any cell surface antigen which is generally associated with tumor cells, i.e., occurring to a greater extent as compared with normal cells. Such antigens may be tumor specific. Alternatively, such antigens may be found on the cell surface of both tumorigenic and non-tumorigenic cells. These antigens need not be tumor specific. However, they are generally more frequently associated with tumor cells than they are associated with normal cells.

As used herein, "pharmaceutically acceptable carrier" includes any material which when combined with the antibody retains the immunogenicity of the antibody and is non-reactive with the immune systems of the subject. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The Invention

The invention provides monospecific antibodies which specifically bind an epitope of a human DPPIV (dipeptidyl peptidase IV/CD26) and inhibits angiogenesis. The monospecific antibodies of the present invention include monoclonal, chimeric and humanized antibodies and antibody fragments that specifically bind the epitopes bound by either of the anti-DPPIV antibodies E19 or E26. In a preferred embodiment the antibody fragments comprise the antigen-binding region of the antibody.

In one embodiment the monospecific antibodies of the present invention include those that bind specifically with the catalytic or substrate-binding domains of human DPPIV (dipeptidyl peptidase IV, also known as CD26).

In another embodiment the antibodies of the present invention specifically bind invadopodia of cells of a tissue undergoing angiogenesis. Such cells may be cancerous cells, cells of a tumor in a human being in vivo, or the cells may be cells may comprise a tissue or an organ undergoing an ex-vivo procedure.

The active antibodies and active antibody fragments of the present invention exhibit one or more of the following characteristics:

i) the antibodies specifically bind to the invadopodia of invasive cells grown in collagen or on fibronectin films,
ii) the antibodies antibody fragments fail to react with non-invasive human carcinoma cells grown in collagen or on fibronectin films.
iii) the antibodies antibody fragments bind weakly to differentiated human endothelial cells in collagen or matrix gels and more strongly to sprouting human endothelial cells in collagen or matrix gels,
iv) the antibodies antibody fragments bind weakly with connective tissue cells and more strongly with these induced by wounding,
v) the antibodies antibody fragments block the interaction of collagen matrix with reactive human cells and inhibit the collagen degradation by such cells and
vi) the antibodies or antibody fragments react readily with the catalytic or substrate binding domains of DPPIV and of the seprase-DPPIV complex.

The antibodies of the present invention may comprise a seprase-DPPIV antagonist for use in the present methods. Such seprase-DPPIV antagonists are capable of binding to the catalytic and substrate-binding domains and competitively inhibiting the ability of seprase-DPPIV to interact with a natural ligand such as type I or IV collagen. Preferably, the antagonist exhibits specificity for seprase and DPPIV over other proteases, including urokinase and matrix metalloproteases. In a particularly preferred embodiment, a polypeptide or antibody fragment react readily with the catalytic or substrate-binding domains of the seprase-DPPIV complex and inhibits binding of collagen or E19 and E26 monoclonal antibodies to said domains. A preferred seprase-DPPIV antagonist may be a polypeptide or a monoclonal antibody, or functional fragment thereof, that is immunoreactive with either the catalytic or substrate-binding domains (or both) of the seprase-DPPIV complex. In one embodiment the antibody competitively inhibits the peptidase activity of DPPIV.

Also provided by the present invention are bispecific antibodies with binding specificity for two epitopes, one of which is an epitope of DPPIV. The bispecific antibodies of the present invention include those in which the second epitope bound is an epitope of seprase, MT1-MMP, MMP-2 or an integrin, such as $\alpha(3)\beta(1)$-integrin, $\alpha_v\beta_3$-integrin or $\beta1$-integrin. The second epitope may be an epitope of any tumor-associated antigen.

The present invention further provides immunoconjugates comprising a monospecific antibody which specifically binds an epitope of human DPPIV and inhibits angiogenesis, joined to a therapeutic agent. These immunoconjugates include those which comprises the monoclonal antibodies E19 or E26 or fragments of such antibodies. In a preferred embodiment the immunoconjugate is capable of killing cells involved in angiogenesis.

Alternatively the immunoconjugates of the present invention may include recombinant, chimeric, or humanized antibodies; or fragments of any of these. The immunoconjugates of the present invention may comprise a therapeutic agent such as an anti-tumor drug, a cytotoxin, a radioactive agent, a photosensitizer, a second antibody or an enzyme.

In yet another aspect the invention provides pharmaceutical compositions for inhibiting angiogenesis comprising an effective amount of a monospecific antibody which specifically binds an epitope of a human DPPIV and inhibits angiogenesis, the antibody being formulated in a pharmaceutically acceptable carrier.

The invention further provides pharmaceutical compositions for inhibiting angiogenesis comprising an effective amount of a bispecific antibody which specifically binds an epitope of a human DPPIV and inhibits angiogenesis, the antibody in a pharmaceutically acceptable carrier.

In yet another aspect the invention-provides pharmaceutical compositions for inhibiting angiogenesis comprising an effective amount of an immunoconjugate of a monospecific or a bispecific antibody which specifically binds an epitope of a human DPPIV and inhibits angiogenesis, the antibody being formulated in a pharmaceutically acceptable carrier.

The present invention yet further provides a method of treating a patient suffering from a growth or proliferative disorder involving angiogenesis, comprising administering an effective amount of a monospecific antibody which specifically binds an epitope of a human DPPIV and inhibits angiogenesis.

The present invention also provides a method of treating a patient suffering from a growth or proliferative disorder involving angiogenesis, comprising administering to the patient an effective amount of a bispecific antibody which specifically binds an epitope of a human DPPIV and inhibits angiogenesis.

In yet another aspect the present invention provides a method of treating a patient suffering from a growth or proliferative disorder involving angiogenesis, comprising administering an effective amount of an immunoconjugate of a monospecific antibody which specifically binds an epitope of a human DPPIV and inhibits angiogenesis.

The present invention further provides a method of treating a patient suffering from a growth or proliferative disorder involving angiogenesis, comprising administering an effective amount of an immunoconjugate of a bispecific antibody which specifically binds an epitope of a human DPPIV and inhibits angiogenesis.

The anti-angiogenic treatment methods of the invention described above may be applied to patients with solid tumors, preferably to inhibit angiogenesis and metastasis, and most preferably to induce tumor regression. More preferably still, the treatment methods are capable of curing the patient of the tumor such that tumor regression is substantially complete.

Also provided are continuing hybridoma cell lines, which secrete recoverable quantities of monoclonal antibodies which specifically bind an epitope of a human DPPIV and inhibit angiogenesis. In a particular embodiment the hybridoma is one that produces a monoclonal antibody of the class $IgG_{2a}$, designated E19. In another particular embodiment the hybridoma is one that produces a monoclonal antibody of the class $IgG_{2a}$, designated E26.

The invention relates to a membrane protease complex, consisting of two homodimers of seprase and dipeptidyl peptidase IV (DPPIV), initially obtained from human placental capillary endothelial membranes, monoclonal antibodies against components of the complex and a method of inhibiting capillary sprouting and angiogenesis in human cancer.

Two novel rat monoclonal antibodies of the class IgG.2a react readily with the protease complex consisting of seprase and DPPIV that resides on cell surface invadopodia at the leading edge of angiogenic endothelia, migratory fibroblasts, and invading cancer cells. These antibodies fail to react with resting cells in adjacent human tissues and blood vessels. They also block interaction of collagen matrix with the seprase-DPPIV complex in the invasive cells during angiogenesis and cancer spreading but not that with other endothelia or tumor cells not undergoing angiogenesis.

The disclosures of the present invention herein demonstrates that angiogenesis in tissues requires a membrane protease complex, consisting of two homodimers of seprase and dipeptidyl peptidase IV (DPPIV), and that inhibitors of the seprase-DPPIV complex can inhibit angiogenesis. The disclosure also demonstrates that antagonists of two novel rat monoclonal antibodies of the class IgG.2a react readily with the catalytic and substrate-binding domains of the protease complex that resides on cell surface invadopodia at the leading edge of angiogenic endothelia, migratory fibroblasts, and invading cancer cells, while failing to react with resting cells in adjacent human tissues and blood vessels. These antibodies have the property of blocking interaction of collagen matrix with the seprase-DPPIV complex in the invasive cells during angiogenesis and cancer spreading but not that with other endothelia or tumor cells.

The invention describes methods for inhibiting angiogenesis and cancer metastasis in a mammalian tissue comprising administering to the mammal a composition comprising an effective amount of a seprase-DPPIV antagonist such as monoclonal antibody E19 or E26.

The methods of the present invention are applicable to any mammal. Mammals include, for example, laboratory animals such as rats, mice and guinea pigs; farm animals such as cows, horses, sheep and goats; pet animals such as dogs and cats; primates such as apes and monkeys; and most preferably, human patients.

The tissue to be treated can be any tissue in which inhibition of angiogenesis or cell invasion is desirable, such as diseased tissue where neo-vascularization or cancer spreading is occurring. Exemplary mammalian, particularly human tissues include various types of carcinomas, metastases, tissues undergoing restenosis, inflamed tissue, and the like.

A seprase-DPPIV antagonist for use in the present methods is capable of binding to the catalytic and substrate-binding domains and competitively inhibiting the ability of seprase-DPPIV to interact with a natural ligand such as type I or IV collagen. Preferably, the antagonist exhibits specificity for seprase and DPPIV over other proteases, including urokinase and matrix metalloproteases. In a particularly preferred embodiment, a polypeptide or antibody fragment react readily with the catalytic or substrate-binding domains of the seprase-DPPIV complex and inhibits binding of collagen or E19 and E26 monoclonal antibodies to said domains. A preferred seprase-DPPIV antagonist can be a polypeptide or a monoclonal antibody, or functional fragment thereof, that immunoreacts with the catalytic or substrate-binding domains of the seprase-DPPIV complex.

Seprase and DPPIV are activated on specialized protrusions (invadopodia) of migratory endothelial cells. Both seprase and DPPIV are transiently expressed in endothelial cells at sites of sprouting vessels but not in differentiated vessels in human breast cancer tissue or in human angiogenesis models. In contrast, other known targets for anti-angiogenesis therapies which include $\beta 1$-integrins, MT1-MMP and MMP-2 are constitutively expressed in endothelial cells. Antibodies to DPPIV block endothelial migration and sprouting but do not affect preexisting capillaries; whereas $\beta 1$-integrin antibodies or MMP inhibitors strongly disturb both processes. Because seprase and DPPIV are co-expressed at very low levels in differentiated endothelium, they make attractive new therapeutic targets for cancer angiogenesis.

In another aspect, the invention provides a method of stimulating angiogenesis in a mammal suffering from disease or disorder that may be remedied by an increased blood supply. The disease or disorder may be any disease or disorder in which the blood supply in at least one tissue is reduced or restricted. There are many such diseases and disorders. For instance, one such disease is cardiovascular disease, in which the blood supply to heart muscle tissue may be reduced or severely restricted. The method provided by the present invention causes stimulation of angiogenesis in the afflicted mammal by administering an angiogenesis-stimulating amount of a DPPIV stimulator, thereby increasing the blood supply to the affected tissue.

A DPPIV stimulator, according to the present invention is any compound that enhances the activity or expression of the DPPIV peptidase. Stimulation caused by the DPPIV stimulator may be by any mechanism. This may be by stimulation of the activity of DPPIV by the DPPIV stimulator acting as an agonist. Alternatively, the stimulation may be achieved by increased expression of the DPPIV peptidase.

The rat hybridoma that produces monoclonal antibody E26 was deposited with American Type Culture Collection, 10801 University Blvd., Manassas, Va. 20110 on May 15, 2001 under the terms of the Budapest Treaty and assigned patent deposit accession number PTA-3377. The rat hybridoma that produces monoclonal antibody E19 was deposited with American Type Culture Collection, 10801 University Blvd., Manassas, Va. 20110 on May 15, 2001 under the terms of the Budapest Treaty and assigned patent deposit accession number PTA-3378.

EXAMPLES

Methods: Following methods were carried out as described: immunohistological staining of tissue sections (Kelly et al., 1998); seprase/DPPIV protein and proteolytic activity (Pineiro-Sanchez et al., 1997); RT-PCR (Goldstein et al., 1997); double-labeled immunofluorescence of cultured cells and β1-integrin blotting (Mueller et al., 1999), MMP-2 activity (Nakahara et al., 1997); endothelial migration and monolayer wound assays (Pepper et al., 1996); HUVEC (Human umbilical vein endothelial cell) culture and Matrigel® (basement membrane matrix) tube assay (Grant et al., 1992).

Example 1

Cytoimmunohistochemical Staining for Seprase and DPPIV in Endothelial Cells Sprouting Vessels and in Normal Tissue.

To investigate the expression of seprase and DPPIV during angiogenesis, human malignant breast carcinoma tissue or adjacent normal skin were stained with antibodies specific for either seprase or DPPIV. Both seprase and DPPIV were abundantly expressed on the endothelial cells of sprouting vessels (FIG. 1, solid arrows) but were not detectable in other tumor vessels (FIG. 1, open arrows) or in adjacent normal skin from the same donor. These findings indicate that only sprouting sites of blood vessels involved in tumor angiogenesis have enhanced expression of seprase and DPPIV. Consistent with this result, expression of seprase and DPPIV on cultured endothelial cells can be induced by means or factors that enhance cell migration and vessel sprouting (see below).

Example 2

Cytoimmunohistochemical Staining for Seprase and DPPIV in Human Primary Cell Culture Monolayers of Different Cell Densities.

Figure 2A:
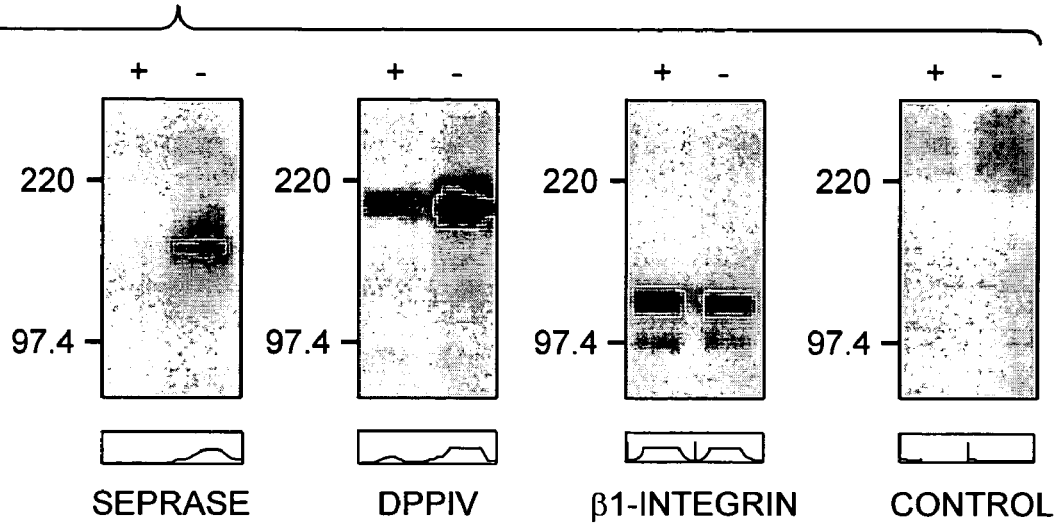
FIG. 2. Enhanced expression and proteolytic activities of seprase and DPPIV in migratory endothelial cells. a–e, Seprase/DPPIV expression, proteolytic activities and mRNA profiles were analyzed in confluent (+) and sparse (−) HUVEC. a, Immunoblotting analysis of cell lysates using anti-seprase (D28, Piniero-Sanchez et al., 1997), DPPIV (E26), β1-integrin (C27, Bloch et al., 19977) and antibody control. The immunoblots and their densitometry scans (adjoining panels) show that both seprase and DPPIV are elevated in sparse cultures, while β1-integrin remains the same in confluent (+) and sparse (−) conditions. b, Gelatin zymography of cell lysates in the presence of Ca++ (+2 mM CaCl₂) and deprived of Ca++ (+2 mM EDTA). The 170-kDa gelatinase (seprase) activity was elevated in sparse cultures, while the 62-kDa MMP-2 activity remained the same in confluent (+) and sparse (−) conditions. c, DPPIV substrate Gly-Pro-AFC (7-Amino-4-Trifluoromethyl Couramin) overlay of cell lysates. The 200-kDa DPPIV activity was increased in the sparse culture. d, Detection of seprase RNA. RT-PCR was carried out on total RNA from LOX human malignant melanoma cells (Lox)—a positive control (Goldstein et al., 1997) and confluent (+) and sparse (−) HUVEC using oligonucleotide primers "FAP1 +2" and "FAP11 +4" that correspond to specific nucleotide positions of the seprase cDNA as described (Goldstein et al., 1997). Minus reverse transcriptase controls are shown in lanes marked "RT". Similar amounts of glyceraldehyde-3-phosphate-dehydrogenase mRNA were detected in both the confluent and sparse HUVEC (Lanes marked GPDH). These results suggest that the increased expression of seprase detected in sparse HUVEC is not due to an upregulation in the seprase mRNA level; but instead is due to increased translational efficiency of the seprase mRNA and/or increased stability of seprase itself. e, Detection of DPPIV RNA. RT-PCR was carried out on total RNA from confluent (+) and sparse (−) HUVEC using oligonucleotide primers DPPF1+DPPR2 that correspond to nucleotide positions #24–43 (5' UTR) and #2798–2781 (3' UTR) in human DPPIV cDNA. f–g, Immunofluorescence distribution of seprase and DPPIV in migratory HUVEC stimulated by wounding (indicated by arrows) of the monolayer (central panels). The wound monolayer was stained three hours later with antibodies against DPPIV (E26) and β1 (C27) or seprase (D28) and β1 (C27), respectively. Bar=10 μm. h, Morphology of HUVEC migration at time 0 and 24 hours after wounding of the monolayer (panels marked 24 hr). The wound was closed within 24 hours but cell migration could be blocked by mAbs E19 or E26 against DPPIV. i, Dose-dependent inhibition of cell migration by inhibitory mAb E19 (against DPPIV;—□ open squares) and C27 (β1; open triangles) but not by control mAb E3 against DPPIV (DPPIV solid triangles) or C37 (against cell surface glycoprotein gp90; solid circles). Three experiments of 4 h monolayer wound models were carried out for each antibody. Cell migration was quantified by measuring the areas of cell advancement from the original wound edge. The values are mean±SD. j, Time-course of antibody inhibition of cell migration. All antibodies, mAb E19 (against DPPIV;—□ open squares), C27 (β1; open triangles), E3 (DPPIV solid triangles), C37 (glycoprotein gp90; solid circles), or buffer alone (Control; solid diamonds) were applied at 5 μg per ml. Experimental conditions were the same as panel i above.
Figure 2B:
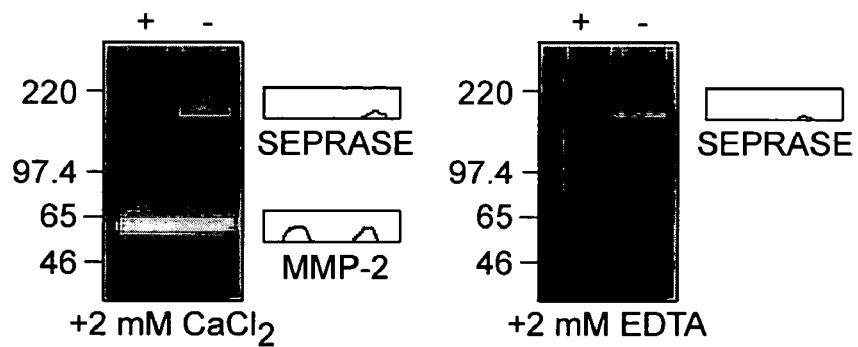
Figure 2C:
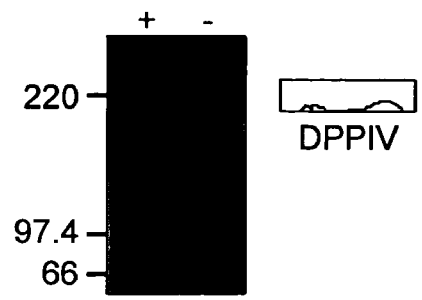

Endothelial cells of sprouting vessels are migratory and exhibit a lack contact inhibition (Pepper et al., 1993). Monolayer cultures of human umbilical vein endothelial cells (HUVEC) can be induced to migrate by wounding or passage to low cell density (Pepper et al., 1996). This assay was used to examine the expression of seprase and DPPIV in migratory endothelial cells. The confluent HUVEC monolayers were found to contain low levels of seprase and DPPIV and their proteolytic activities were also low (FIGS. 2a–c). Passage of monolayers into a sparse culture within 24 hours induced the expression of functional seprase protein; it also caused an increase in DPPIV protein and their proteolytic activities (FIGS. 2a–c).

Figure 2D:
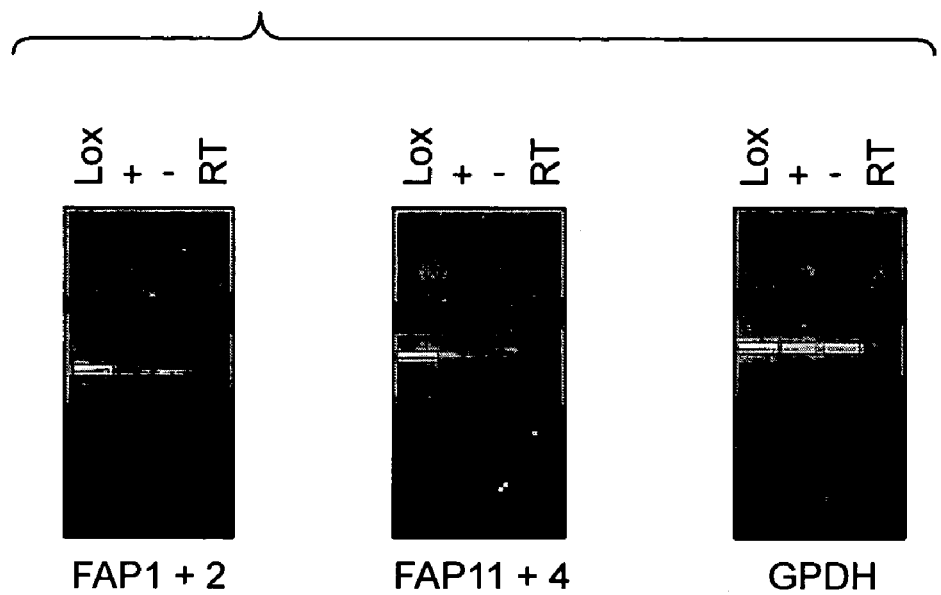
Figure 2E:
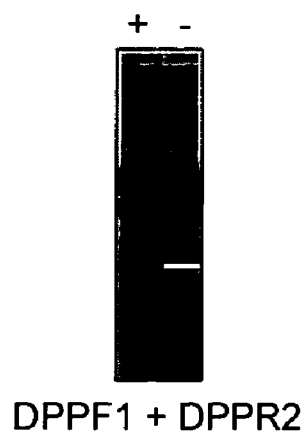

Both HUVEC cultures had detectable seprase and DPPIV mRNA (FIGS. 2d–e). As β1-integrins (Bloch et al., 1997) and membrane-bound MMP-2 (Hiraoka et al., 1998) have been shown to be essential for angiogenesis, we examined their presence in this assay. β1-integrin and MMP-2 gelatinase activity were readily detectable in both confluent and sparse endothelial cultures, while seprase and DPPIV (protein/activity) were increased in the sparse culture (FIGS. 2a–b). The result strongly suggests the association of seprase and DPPIV expression with migratory activity of endothelial cells.

Example 3

Expression of Seprase/DPPIV and β1-Integrins During Wound-Induced Endothelial Migration.

Figure 2F:
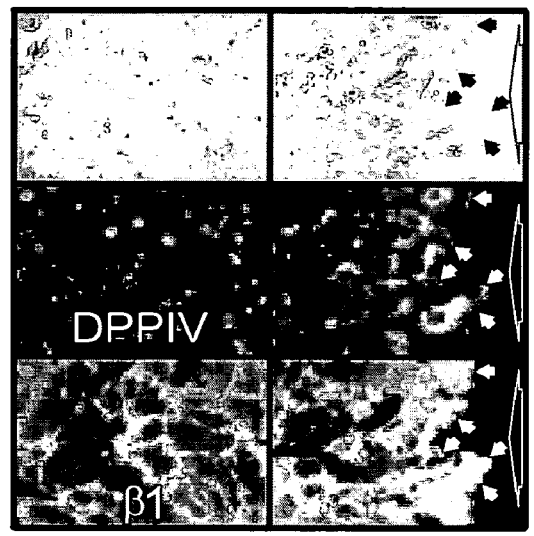
Figure 2G:
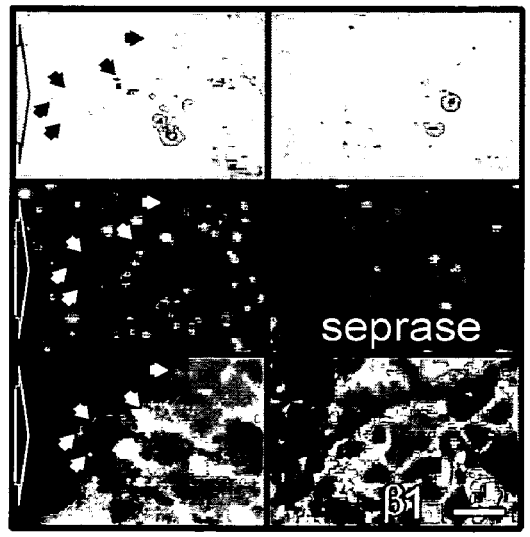

The relative expression of seprase/DPPIV and β1-integrins during wound-induced endothelial migration was examined by double-labeled immunofluorescence. The monolayer wound model consists of a 300 μm width wound on the HUVEC monolayer; migratory activity of HUVEC was visible one hour after wounding (FIGS. 2f–g). Expression of β1-integrins was high in endothelial cells at both the wound edge (wounded) and in the monolayer (stationary); in contrast, seprase and DPPIV expression was restricted to migratory cells at the wound edge (FIGS. 2f–g, arrows).

In addition, seprase and DPPIV expression was found on invadopodia (FIGS. 2f–g, arrows) and on the perinuclear region (Golgi apparatus) of migratory cells but not in confluent cells. In phase contrast images (FIGS. 2f–g), β1-integrins were distributed widely on the surface of migratory cells (FIGS. 2f–g, solid arrows) and particularly concentrated at sites of contact between confluent cells, suggesting the role of integrins in both cell migration and adhesion. Similar to β1, membrane type-1 MMP was found distributed evenly on the cell surface of HUVEC at the wound edge and in stationary monolayers.

Example 4

Inhibitory Effects of Anti-DPPIV mAbs on Cell Migration of Fibroblasts and of Wounded Cells from a Monolayer.

Figure 2H:
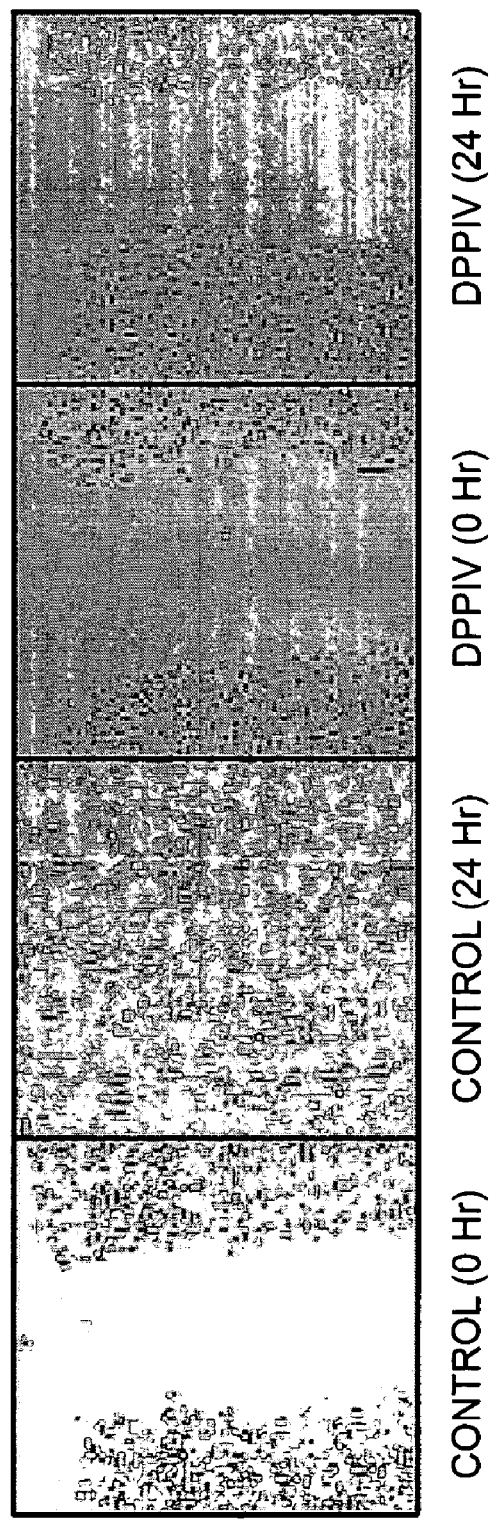
Figure 2I:
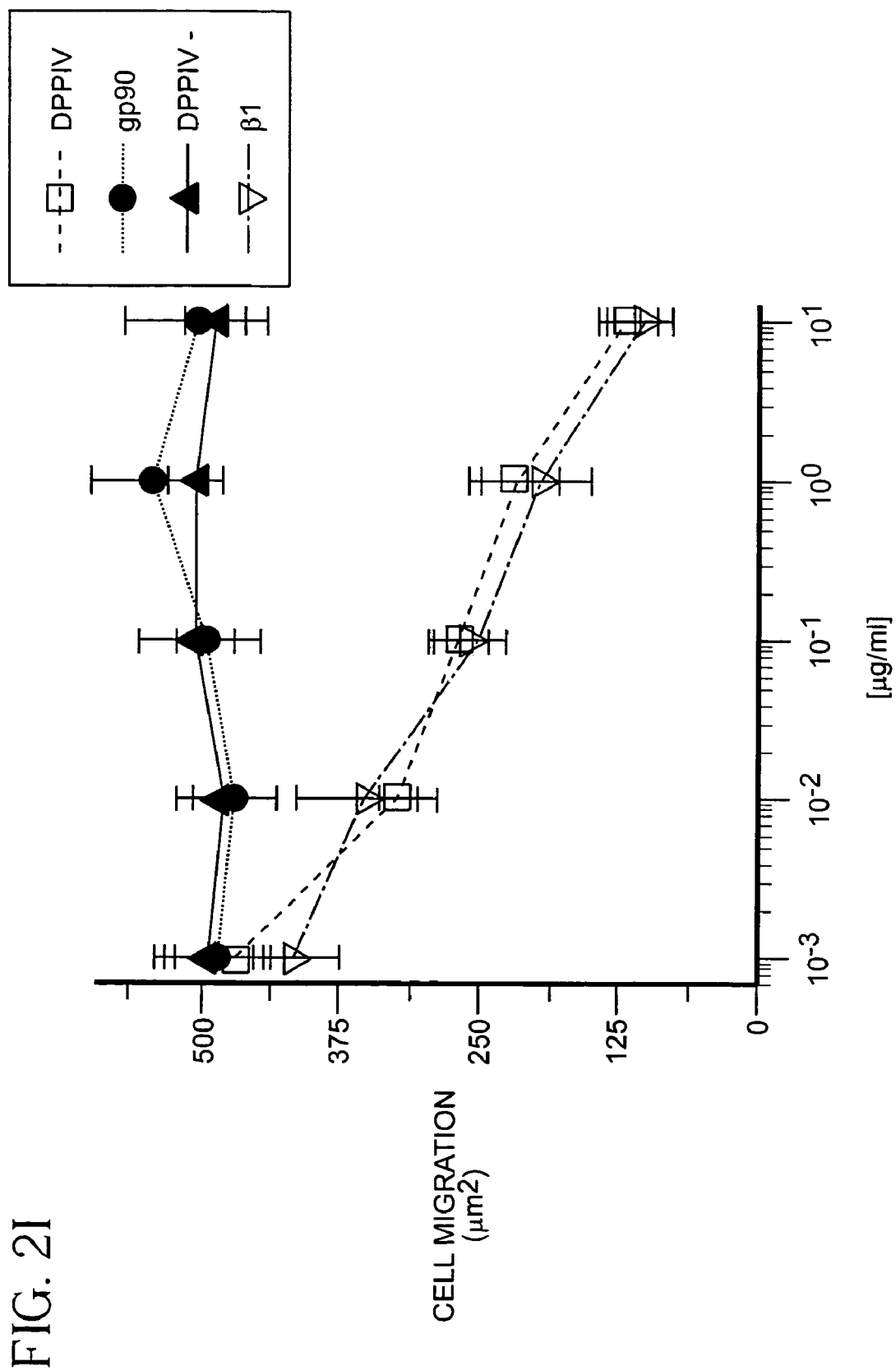
Figure 2J:
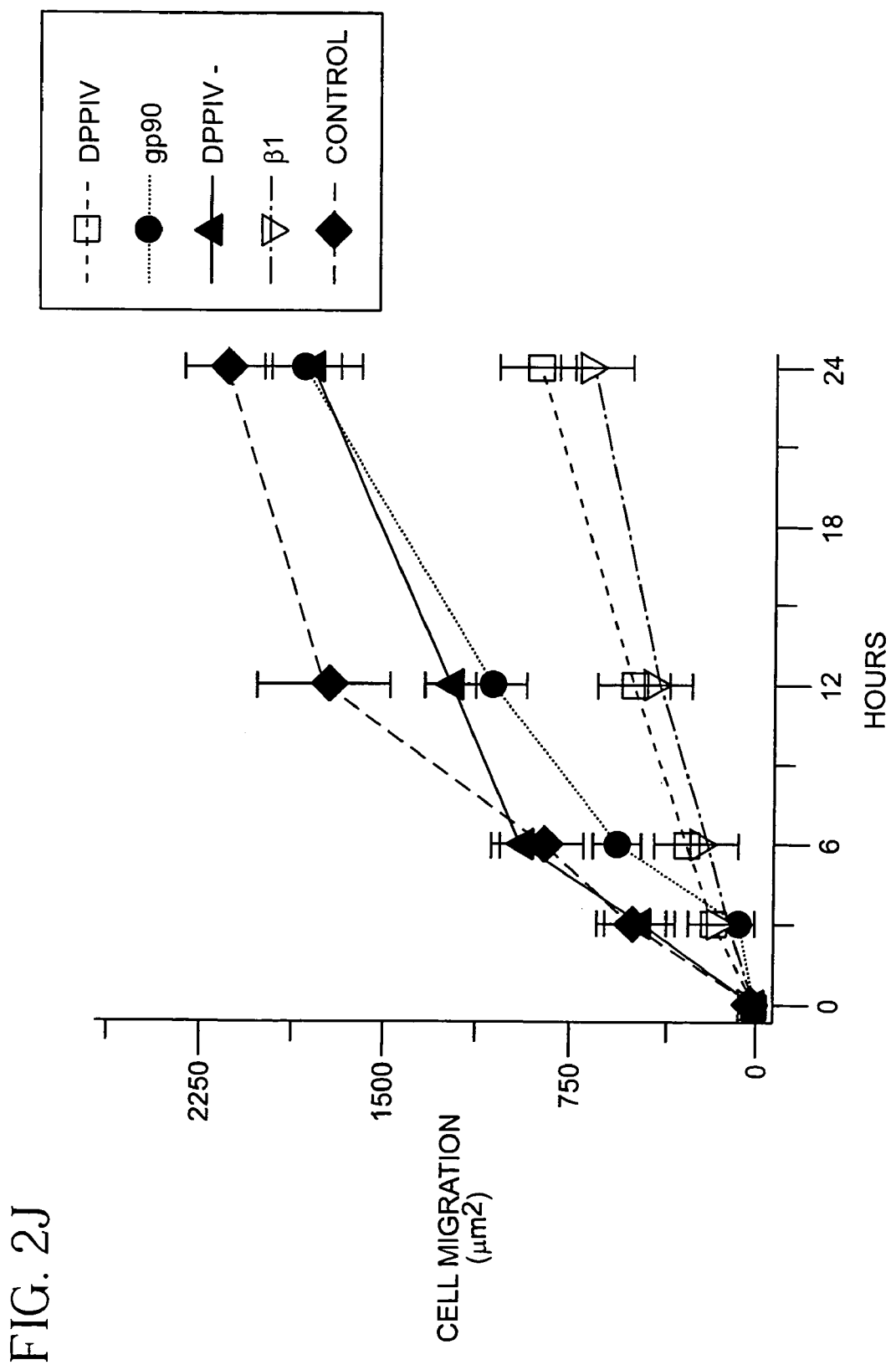

The effect of various mAbs against DPPIV (E19 and E26 are inhibitory; E3 is not), β1-integrins (C27 and 13 are inhibitory), and a cell surface glycoprotein gp90 (C37 is not inhibitory) (Mueller et al., 1999) were examined to determine whether DPPIV (and possibly seprase) plays an active role in endothelial migration. Both anti-DPPIV and anti-β1 mAbs blocked endothelial cell migration, whereas the mAb against cell surface proteins gp90 had no effect (FIGS. 2h–j). Identical results were obtained when fibroblast migration and cell surface collagen degradation were induced by monolayer wounding.

Example 5

Inhibitory Effects of Anti-DPPIV mAbs on Blood Vessel Tube Formation.

Figure 3A:
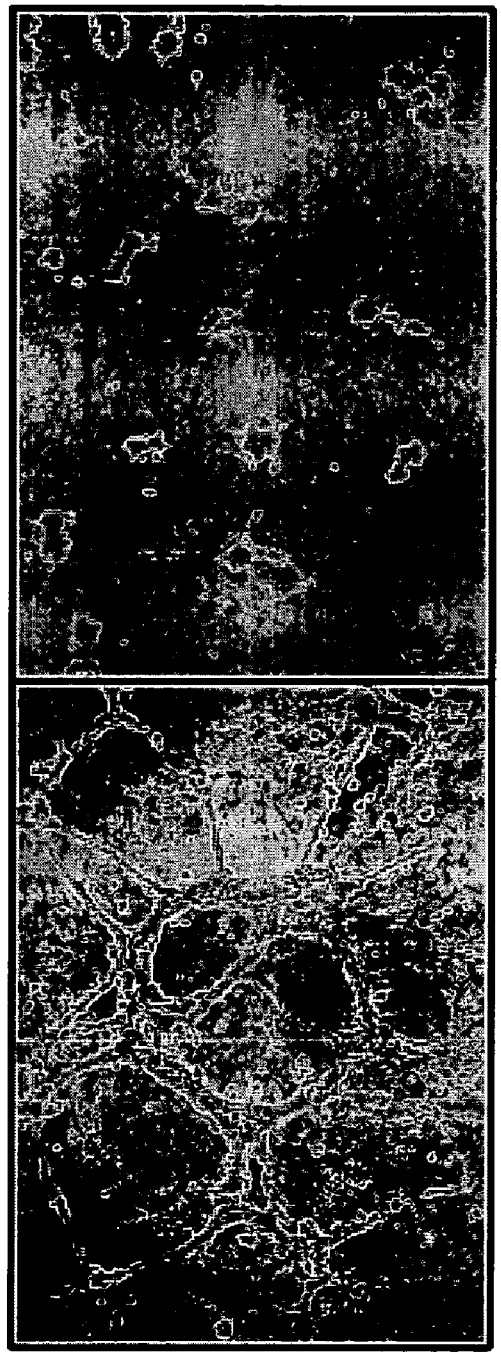
FIG. 3. Inhibition of endothelial tube formation by a mAb to DPPIV. a, Morphology of HUVEC tube formation in Matrigel® (basement membrane matrix) assay (Control). It could be blocked by mAb E19 or E26 (DPPIV). Bar=100 μm. b, Inhibition of endothelial tube formation. All antibodies, mAb E26 (against DPPIV), C27 (β1), E3 or C37 (control IgG), or buffer alone (Control) were applied at 5 μg per ml prior to tube formation when cells adhered to Matrigel® (basement membrane matrix). The matrix metalloprotease inhibitor CT1847 was added at 10 nM in the presence of 0.01% DMSO and 0.01% DMSO was used as vehicle control (+DMSO). Three experiments for each antibody or inhibitor were used in this plot. Tube formation was quantified by measuring the areas of tubes in each well. The values are mean±SD. c, Inhibition of preexisting endothelial tubes by antibodies to DPPIV and β1 or the matrix metalloprotease inhibitor CT1847. Experimental conditions were identical to above except antibodies and inhibitors were applied after tubes were formed. d, Immunofluorescent distribution of seprase in migratory HUVEC (indicated by arrow) from a tube in Matrigel® (basement membrane matrix). The HUVEC culture (phase contrast image shown in the left panel) was stained with antibodies against seprase (D8) (right panel), respectively. Bar=10 μm.
Figure 3B:
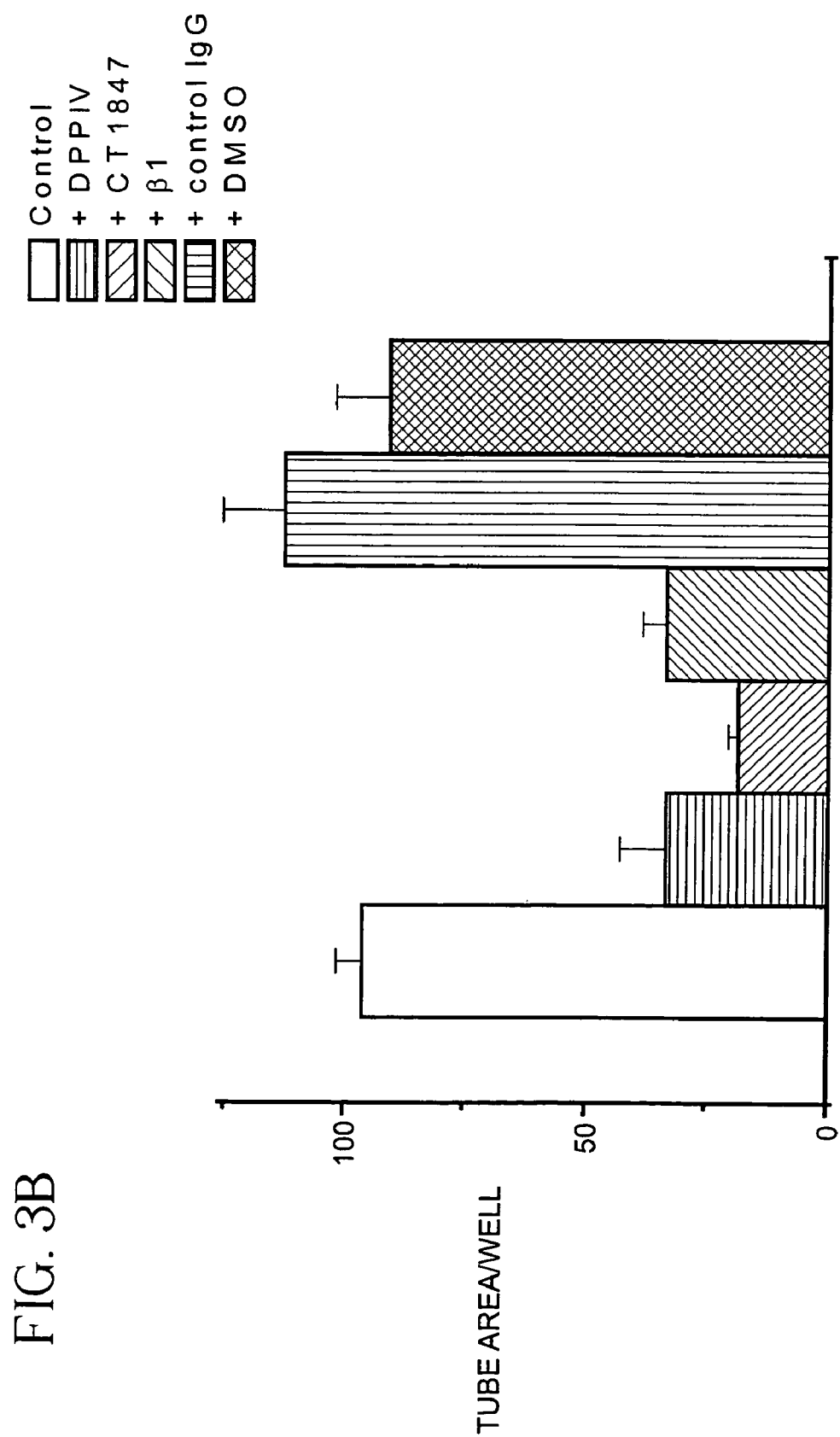
Figure 3C:
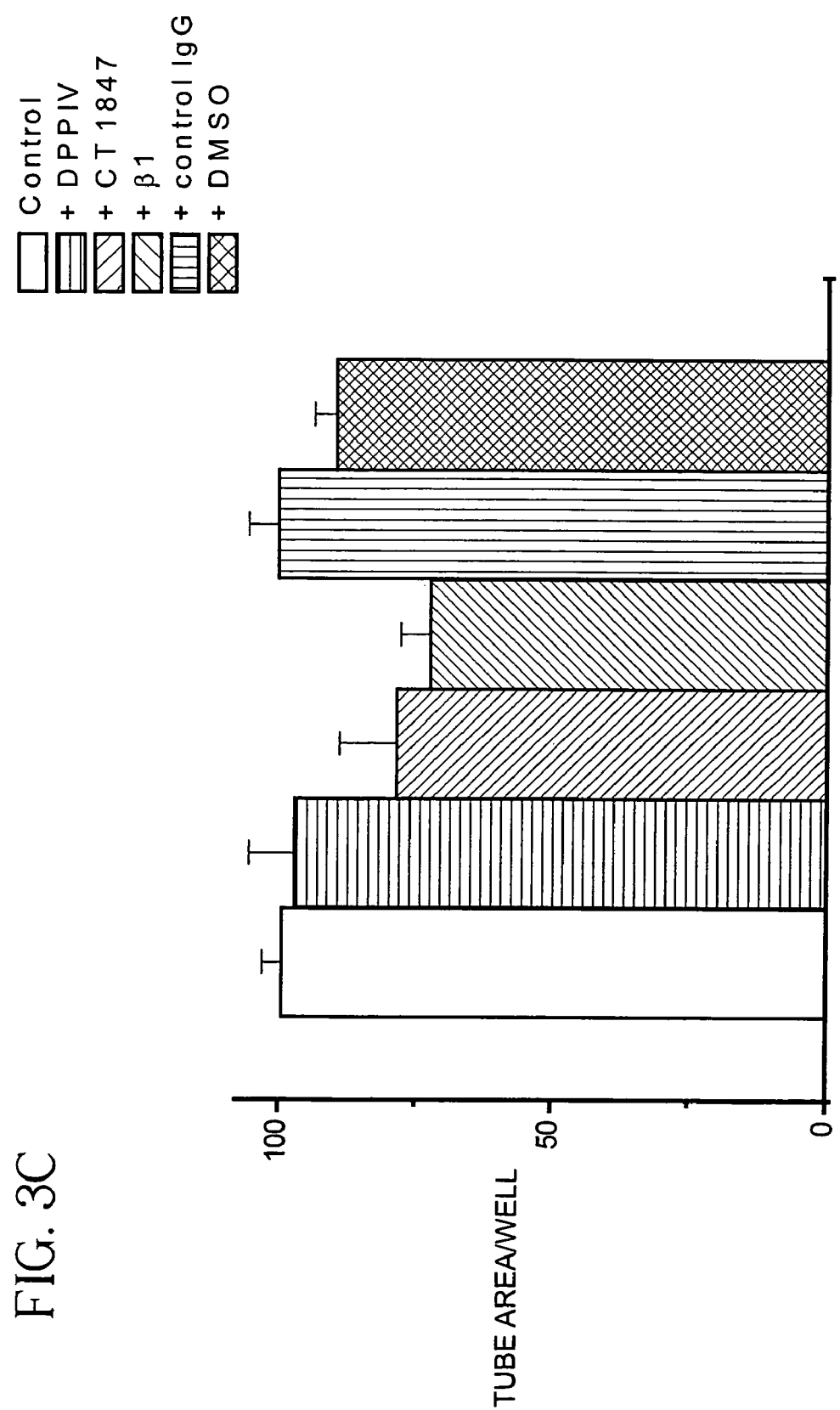
Figure 3D:
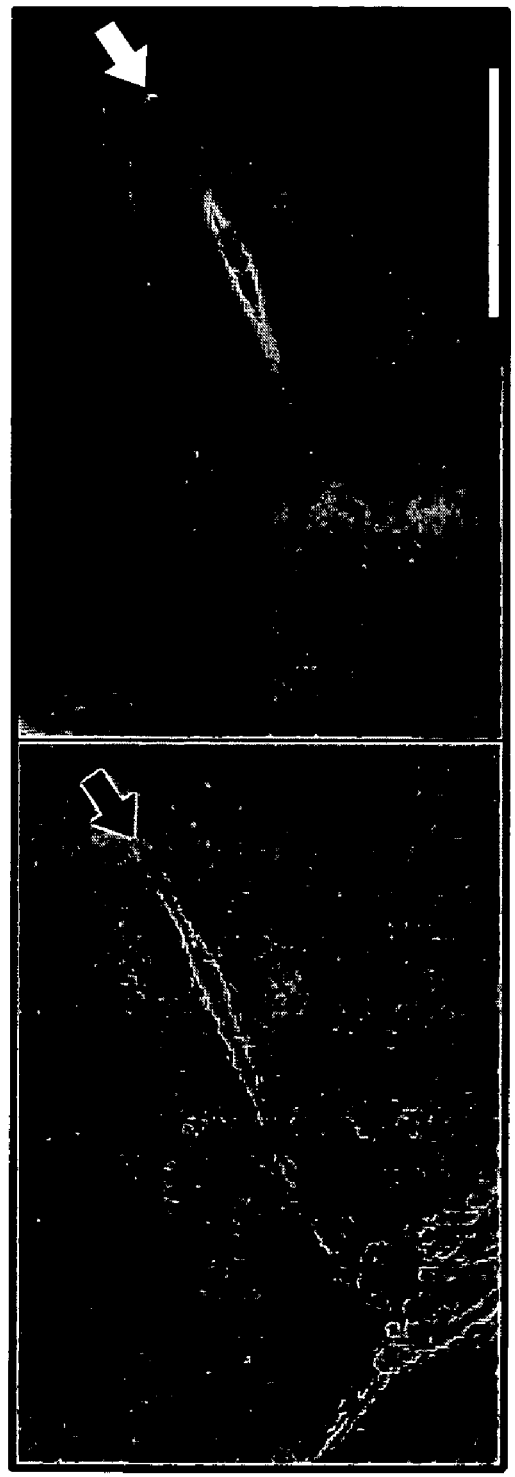

To examine the effects of these same antibodies on endothelial tube formation by Matrigel® (basement membrane matrix) (Grant et al., 1992), mAbs or the matrix metalloprotease inhibitor CT1847 (Zucker et al., 1998) were added prior to or after tube formation (FIG. 3a). The inhibitory anti-DPPIV and β1 mAbs and CT1847 blocked tube formation in Matrigel® (basement membrane matrix) (FIG. 3b); however, only anti-β1 mAb and CT1847 but not the anti-DPPIV mAb perturbed preexisting tubes (FIG. 3c). None of the other mAbs to DPPIV and seprase affected preexisting endothelial tubes. Specific expression of seprase and DPPIV in the endothelial cell migrated from a forming tube (FIG. 3d) also supports the observation that the anti-DPPIV mAb appears to act selectively on new tube formation.

Example 6

Effects of Anti-DPPIV mAbs on Invasion and Capillary Sprout Formation of Human Dermal Microvascular Endothelial Cells (HDMEC).

Figure 4A:
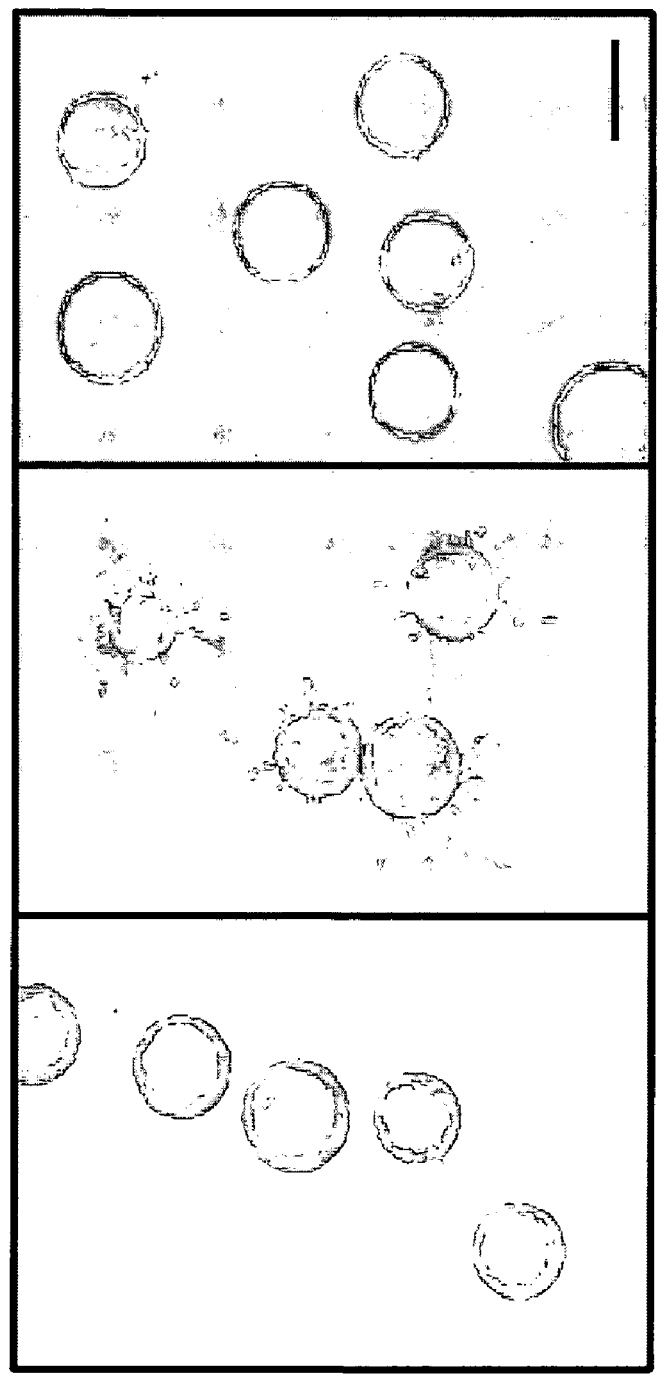
FIG. 4. Inhibition of human angiogenesis in vitro by a mAb to DPPIV. a, Morphology of VEGF- and bFGF-induced HDMEC capillary sprouts and capillary networks (VEGF/bFGF− and +), which could be blocked by mAb E19 or E26 (+DPPIV). Bar=200 μm. b, Inhibition of HDMEC capillary sprouts. All antibodies, mAb E26 (+DPPIV), mAb C27 (+β1), and E3 or C37 (+control IgG), were applied at 20 μg per ml to impregnated fibrin gels. The matrix metalloprotease inhibitor CT1847 was added at 40 nM in the presence of 0.01% DMSO; 0.01% DMSO was used as vehicle control. Three experiments for each antibody or inhibitor were performed in this plot. Capillary sprouting was quantified by measuring the number of tubes and beads in each well. The ratio of tubes/beads occurring with VEGF/bFGF+ samples was arbitrarily set at 100%. The values are mean±SD.
Figure 4B:
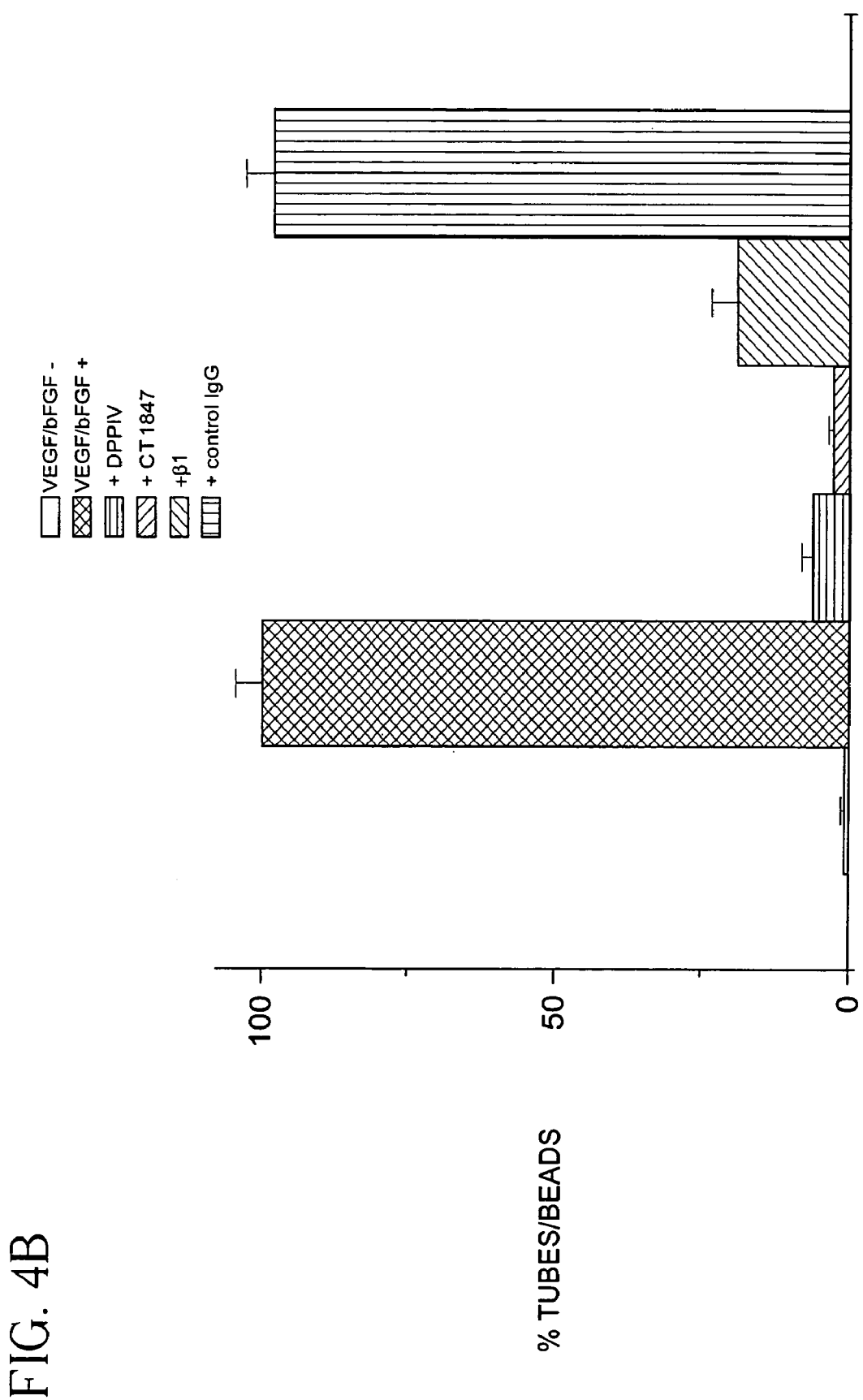

In a recently developed in vitro human angiogenesis model, invasion and capillary sprout formation of HDMEC can be induced in fibrin gels in response to vascular endothelial growth factor (VEGF) and basic fibroblast growth factor (bFGF). This assay was used to determine whether DPPIV plays an active role in human angiogenesis. HDMEC were cultured on microcarrier beads and embedded in a three dimensional human fibrin gel that contained VEGF and bFGF. In this model, HDMEC formed capillary sprouts [within 24 hours] (FIG. 4a, upper pictures labeled with VEGF/bFGF+ or −). The presence of a capillary lumen was confirmed by confocal microscopy. When the fibrin gel was impregnated with the inhibitory anti-DPPIV or β1 antibodies or CT1847, capillary sprouting was blocked (FIGS. 4a–b).

Example 7

The Active Domain of the Seprase-DPPIV Complex.

Recent cloning studies (Goldstein et al., 1997) show that seprase carboxyl terminus contains a putative catalytic region (~200 amino acids), which is homologous (68% identity) to that of the non-classical serine peptidase DPPIV. The conserved serine protease motif G-X-S-X-G (SEQ. ID. NO: 1) is present as G-W-S-Y-G (SEQ. ID. NO: 2). Like DPPIV, seprase have 12 Cys with 6 residues being conserved in the Cys rich region and 3 in the catalytic region. Seprase has a peculiar protease inhibitor profile: it is inhibited by the protease inhibitors, including PMSF and NEM (Aoyama and Chen, 1990). Its gelatinase activity was completely blocked by the serine-protease inhibitors, DFP, PMSF, AEBSF, and APSF. Dimeric seprase could be affinity-labeled by [$^3$H]-DFP but the proteolytically inactive 97-kDa subunit could not (Pineiro-Sanchez et al., 1997). The inhibitor and substrate specificity of the seprase-DPPIV complex isolated from human breast carcinoma cells was analyzed by [$^3$H]-DFP labeling. The method is extremely sensitive in detecting serine proteases and esterases ($10^{-13}$ M) and is based upon the stoichiometrical, covalent binding of [$^3$H]-DFP into the proteases that are reduced in the presence of their substrates and inhibitors. Both dimeric seprase and DPPIV may be labeled with [$^3$H]-DFP and their molecular identity may be visualized on SDS gels (Pineiro-Sanchez et al., 1997). By incubating the seprase-DPPIV complex with [$^3$H]-DFP in the presence of their peptide-substrates or inhibitors, the protease inhibition is quantified.

Seprase and the seprase-DPPIV complex were purified from $10^{11}$ LOX human malignant melanoma cells or MDA-MB-436 human breast carcinoma cells that express seprase and the seprase-DPPIV complex, respectively. Cell lysates are subjected to two steps of enrichment (Triton X-114 detergent phase partitioning and WGA chromatography) and they are stored at −80° C. Purified seprase is prepared immediately prior to experimentation by immunoprecipitation of LOX WGA-binding proteins with micro-magnetic beads (about 50 nm, Miltenyi Biotec) using mAb D28 or D8. The seprase-DPPIV complex is purified from MDA-MB436 WGA proteins with either anti-seprase- or anti-DPPIV-monoclonal antibodies. Purified seprase and the seprase-DPPIV complexes are used to define inhibitor-specificity and substrate-specificity of the enzymes.

Example 8

Substrate Specificity of the Seprase-DPPIV Complex that was Purified by Monoclonal Antibodies.

Collagen-substrate specificity of the seprase-DPPIV complex was determined by incubating fluorescently labeled type I collagen with isolated seprase, DPPIV or seprase-DPPIV complex in the presence of SIMP inhibitors (PMSF inhibits seprase activity and it can be used as control). Briefly, fluorescently labeled collagen was incubated with seprase, DPPIV or seprase-DPPIV complex immobilized on mAb-beads at 37° C., in the presence or absence of enzyme inhibitors. The cleavage site of type I collagen by isolated seprase, DPPIV or seprase-DPPIV was examined. Rates of cleavage and fragment sizes was analyzed by SDS-PAGE as shown in a previous paper (Pineiro-Sanchez et al., 1997). Cleavage products, transferred to an Immobilon-P membrane was subjected to limited sequence analysis to determine the primary cleavage site(s) (Pineiro-Sanchez et al., 1997). The seprase-cleavage peptides include proline and hydroxyproline.

Example 9

X-Proline Dipeptide Bonds as Cleavage Sites of Seprase and Seprase-DPPIV Complex.

Figure 5:
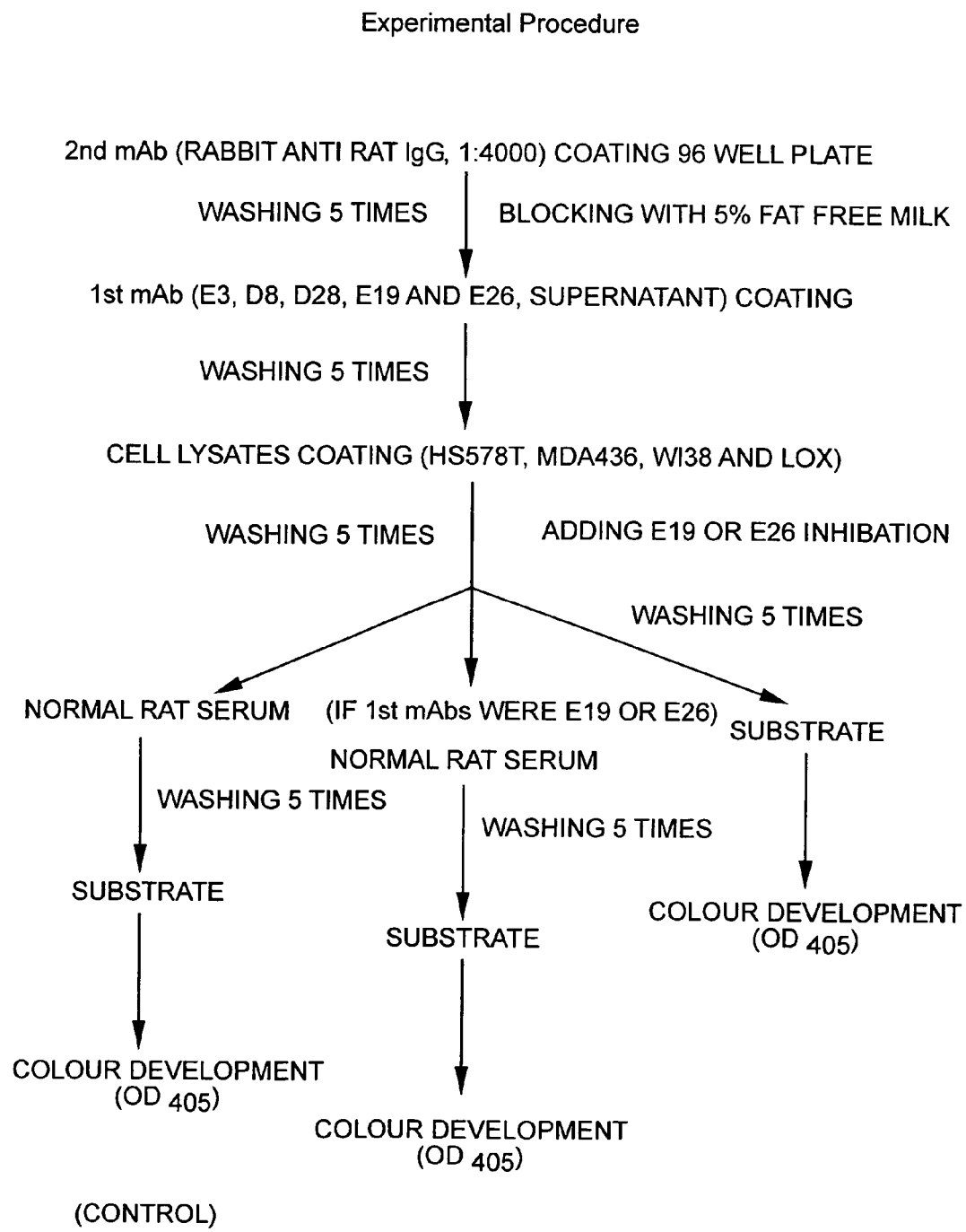
FIG. 5. Experimental procedure for DPPIV/Seprase antigen capture and inhibition assay. Plates were coated with rabbit anti-rat IgG (1:4000 dilution) in blocking buffer (5% fat free milk in 1×PBS)and washed (in washing buffer: 0.05% Tween-20 in 1×PBS). The wells were then incubated with the capture antibody (E3-anti-DPPIV, D8-anti-seprase, D28-anti-seprase, or normal rat serum=supernatant). Alternatively, wells were then incubated with an inhibitory anti-DPPIV antibody E19, or E26 as capture antibody. Wells were washed 5× and incubated with second antibody and again washed 5×. Cell lysates (HS578T, MDA436, WI38 or LOX) or lysates pretreated with anti-DPPIV antibody E19 or E26 were incubated in coated wells, washed and assayed for DPPIV peptidase activity. Antibody reactions were carried out at 37° C. for 4 hrs. DPPIV peptidase assays were developed with chromogenic substrate Gly-Pro-pNA (2.15 mM) or fluorogenic substrate Gly-Pro-AMC (14.6 mM).
Figure 6A:
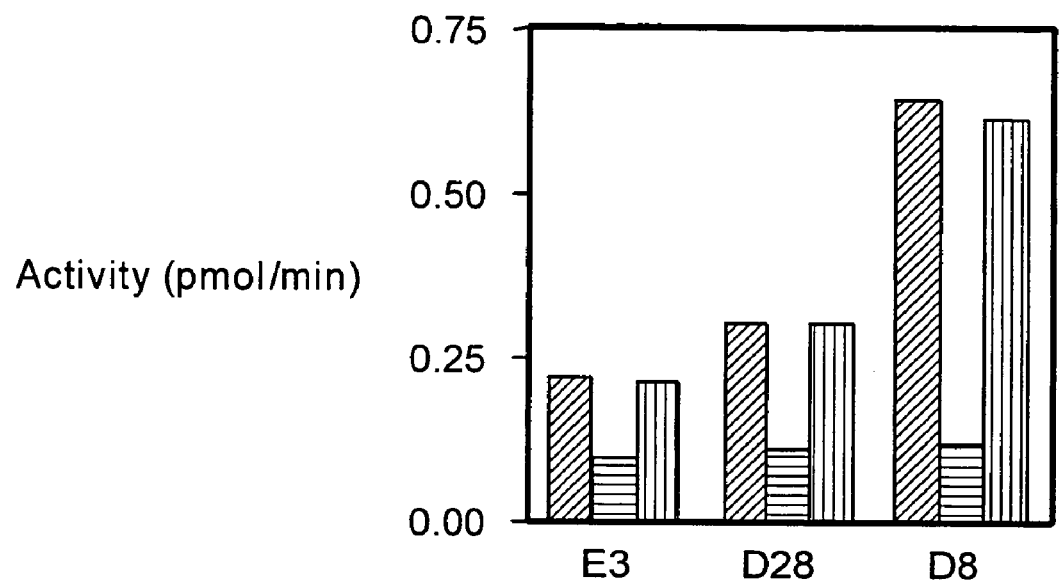
FIG. 6: HS578T and LOX cell lysate DPPIV activity inhibition by mAb E19 or mAb E26. DPPIV activity from cell lysates HS578T (panels A and B) or LOX (panels C and D) measured after antibody binding: with E9 (panels A and C) or E26 (panels B and D). Control: (lightly shaded columns), the 96well plate was first coated with rabbit anti-rat IgG, washed 5× and then coated with the first mAb. Lysates were then bound. Direct inhibition: (black columns) the 96 well plate was first coated with rabbit anti-rat IgG, washed 5× and then coated directly with E19 or E26. Lysates were then bound. Indirect inhibition (medium shaded columns) the 96 well plate was first coated with rabbit anti-rat IgG, washed 5× and then coated with the anti-seprase/DPPIV mAb. Lysates were then bound. After washing, E19 or E26 was added and assayed for peptidase activity.
Figure 6B:
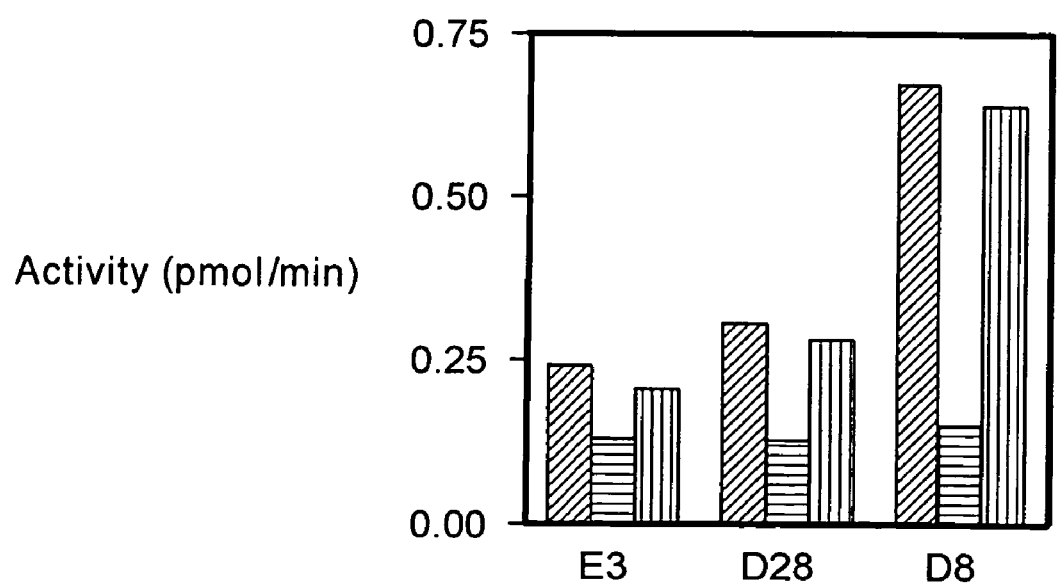
Figure 6C:
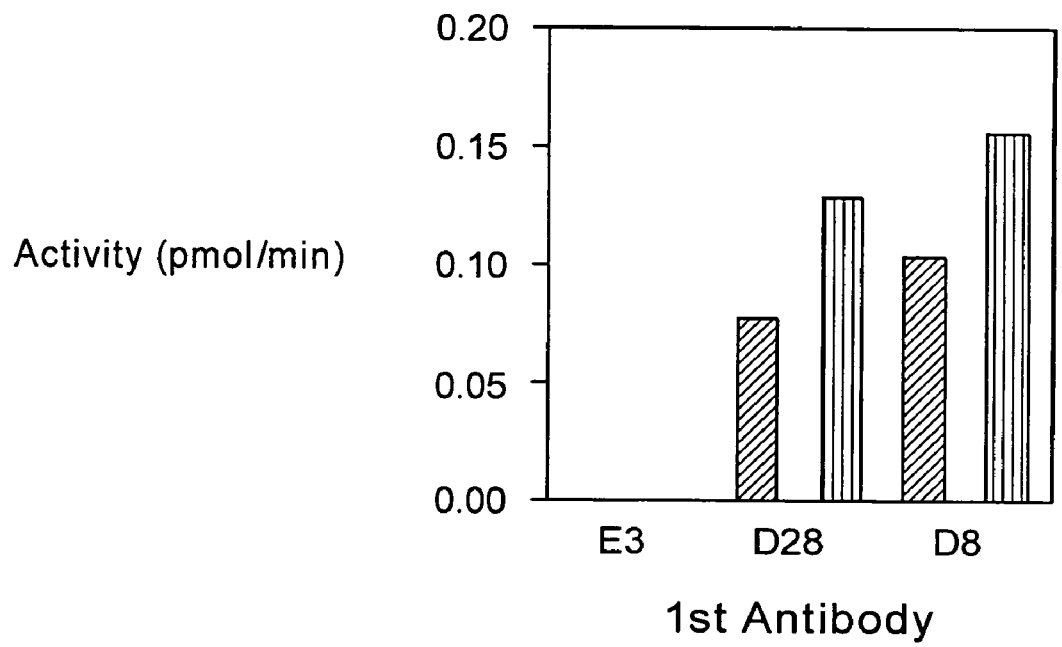
Figure 6D:
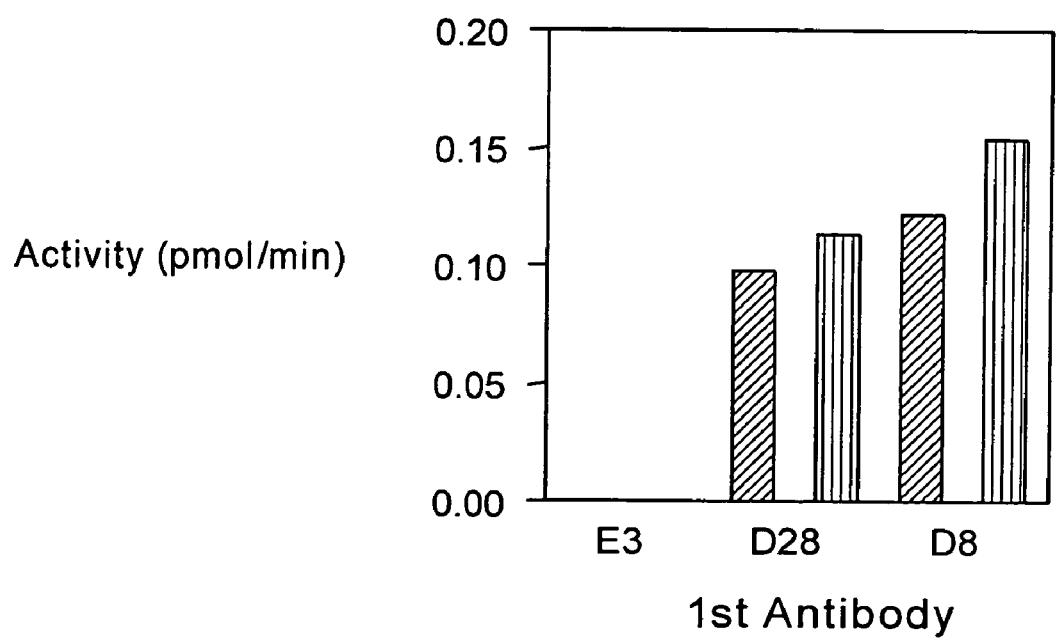
Figure 7A:
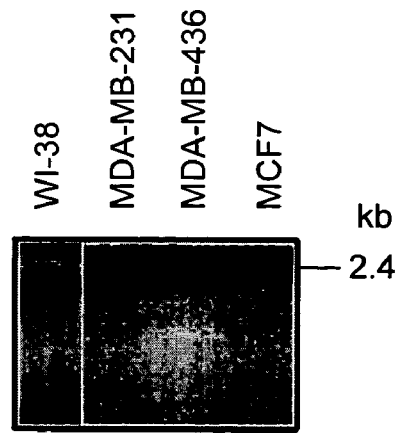
FIG. 7. The detection of mRNA and protein expression of seprase and DPPIV in MDA-MB-436, MDA-MB-231, and MCF7 breast cancer cells by RT-PCR and Western immunoblotting analyses. A and B, RT-PCR was carried out on MDA-MB-231, MDA-MB-436 and MCF7 RNAs using DPPIV and seprase specific primers, respectively. Only MDA-MB-436 cells could be shown to produce the seprase PCR product of ~2.4 kb, which encodes 97-kDa subunit (A). Human WI-38 fibroblast RNA, used as a positive control, generated an identical amplicon pattern as the MDA-MB-436 breast carcinoma cells. A DPPIV PCR product of ~2.8 kb, which encodes the 110-kDa subunit, was detected in the positive control WI-38, andfrom MDA-MB-436 and MCF7 RNAs on agarose gels containing ethidium bromide (B). The two intense lower bands detected in the MCF7 lane were also present in the minus reverse transcriptase control (data not shown). C–E, Western immunoblotting analysis of seprase and DDPIV expression in breast carcinoma cells using the mAbs: D8 and E97 directed against seprase and E19 against DPPIV. The mAb D8 recognizes both seprase and the 97-kDa subunit (C), but mAb E97 recognizes only the monomeric 97-kDa subunit (D) and reveals better total seprase in the cell lysate. Similar to RT-PCR analysis, only MDA-MB-436 cells expressed seprase (C and D), while both MDA-MB-436 and MCF7 breast carcinoma cells expressed DDPIV (E). The mAb D8 recognized the 170-kDa seprase and its 97-kDa subunit in the MDA-MB-436 breast carcinoma cells under nonreduced and nonboiled conditions (F, lane 1), whereas only 97-kDa protein was observed under reduced and boiled conditions (F, lane 2).
Figure 7B:
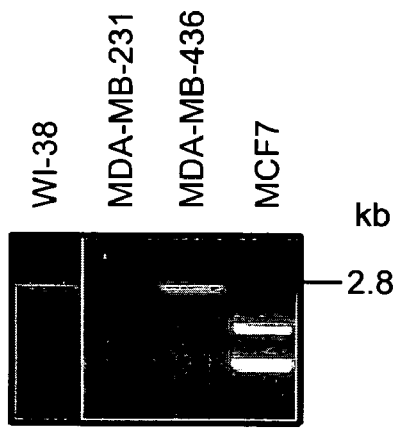
Figure 7C:
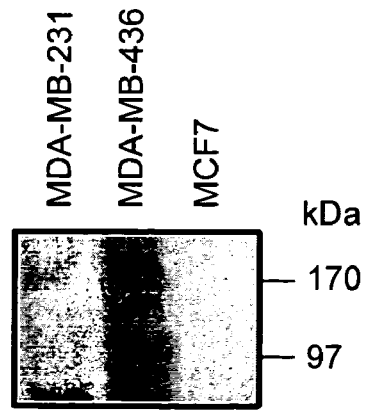
Figure 7D:
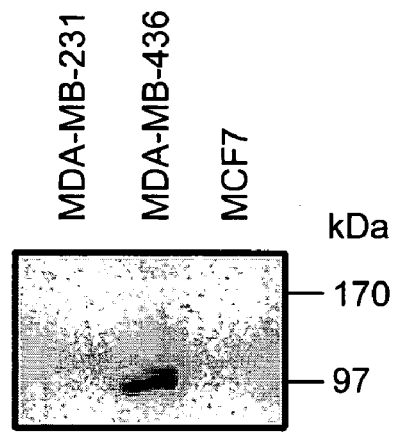
Figure 7E:
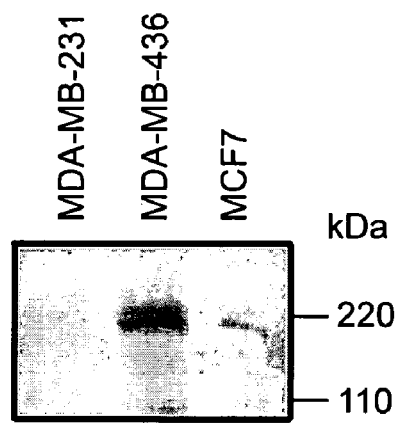
Figure 7F:
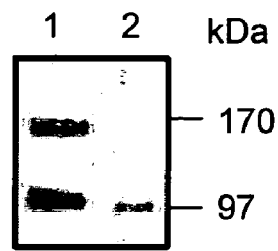

Amino acid cleavage site of individual seprase or the seprase-DPPIV complex were identified to be at X-proline dipeptide bond using method described in a previous paper (Pineiro-Sanchez et al., 1997). Classical DPPIV activity using the fluorescent Ala-Pro-AFC substrate overlay assay showed that SDS-denatured seprase or the protease complex exhibited little activity. However, native seprase and the protease complex purified by monoclonal antibodies from LOX or MDA-MB-436 or Hs578T tumor cells show strong activity toward glycine-proline or alanine-proline etc (X-proline) dipeptide bonds. See FIGS. 5 and 6 and the descriptions of the figures for details. In addition, the figures show that mAbs E19 and E26 interfered with the glycine-proline cleavage by LOX- or Hs578T-seprase complex purified by monoclonal antibodies.

Seprase degrades denatured collagens that contain high levels of proline peptides. Its catalytic domain sequence is highly homologous to that of the proline-specific exopeptidase DPPIV. Seprase and the seprase-DPPIV complex cleaves proline-peptide bonds including for example the following:

(omega-N-(O-acyl)hydroxy amid) aminodicarboxylic acid pyrrolidides (Demuth et al., 1993) and substrates containing phosphorylated residues adjacent to proline (Kaspari et al., 1996), which are potent inhibitors of proline-specific peptidases.

H-Ile-Pro-NHO-pNB, irreversible suicide DPPIV inhibitor
H-Ile-Thia, reversible DPPIV inhibitor (Ki=8×10$^{-8}$)
H-Glu(NHO-Bz)-Pyrr, reversible DPPIV inhibitor (Ki=5×10$^{-7}$)
H-Glu(Gly5)-Thia, reversible DPPIV inhibitor (Ki=8×10$^{-8}$)
H-Pro-Ile-Thia, reversible PEP inhibitor
pGlu-Ile-Thia, reversible PEP inhibitor
Boc-Ile-Pyrr, reversible PEP inhibitor
Boc-Glu(NHO-Bz)-Pyrr, reversible, slowly acylating PEP inhibitor
Z-Phe-Ala-CMK, irreversible PEP inhibitor
Z-Gly-Pro-AMC, fluorogenic PEP substrate
H-Gly-Pro-AMC, fluorogenic DPPIV substrate.

Thus, small or large molecules interfering the interaction of seprase or the protease complex with X-proline in collagen have inhibitory activity for the seprase-DPPIV complex.

Example 10

Phage Displayed Peptides that Recognize Specific Sites of the Seprase-DPPIV Complex that was Purified by Monoclonal Antibodies.

Small peptides that specifically recognize the active sites of the seprase-DPPIV complex are identified using libraries of phage display peptides originally designed by George Smith (Scott and Smith, 1990). Using seprase or the seprase-DPPIV complex purified by mAbs E19 and D8, tens of billions of short peptides are screened and selected for tight binding to specific proteases. The library is a mixture of a vast number of filamentous phage clones, each displaying one peptide sequence on the virion surface. The selection is accomplished by using the above protease preparations to affinity-purify phages that display tight-binding peptides and propagating the purified phage in E. coli. The amino acid sequences of the peptides displayed on the phage are then determined by sequencing the corresponding coding region in the viral DNAs. Specific peptides, displayed on filamentous phages that (i) bind to isolated enzyme or proteins, (ii) block enzymatic activity, and (iii) bind to inhibitory antibodies E19 and E26 against DPPIV are selected.

Such peptides that are recognized by monoclonal antibodies E19 or E26 may lead to the identification of a novel epitope involved in activity of the protease complex. For panning on monoclonal antibodies in (iii) above, inhibitory protease complex mAbs E19 and E26 are used to screen peptides from a random peptide library of 15 amino-acid residues as the approach previously used in the identification of human hepatitis B virus surface epitopes (Motti et al., 1994). The peptides recognized by the mAbs are analyzed for their amino acid similarity to the natural protease antigens, and the selected phage-displayed epitopes behave as antigenic mimics.

Example 11

Identification of Substrates for the Seprase-DPPIV Complex Using Bacteriophage Peptide Display Libraries and Monoclonal Antibody Purification of the Protease Complex.

Potential peptide substrates for seprase or the seprase-DPPIV complex are also identified using bacteriophage peptide display libraries that have been used by Navre's group to identify peptide substrates for stromelysin and matrilysin (Smith et al., 1995). The random hexamer library in the fd-derived vector fAFF-1 included a "tether" sequence that is recognized by monoclonal antibodies. The phage library is treated in solution with seprase or the seprase-DPPIV complex. Cleaved phage is separated from uncleaved phage using a mixture of tether-binding monoclonal antibodies and Protein A-bearing cells followed by precipitation. Clones are screened by the use of a rapid "dot-blot-proteolysis" assay as described in the above reference that identifies phage encoding peptide sequences susceptible to cleavage by the enzyme. The nucleotide sequence of the random hexamer region of isolated clones are determined. Synthetic peptides then are prepared whose sequences are based on some of the positive clones, as well as consensus sequences built from the positive clones. Seprase or specific seprase-DPPIV substrates that are both the most active and smallest are selected. The peptide substrates are used to conjugate with fluorescent AMC, which in turn will be used in search for potential inhibitors using other phage peptide display libraries.

Example 12

General Procedure for Conjugating Small Molecular Drugs to an Antibody.

Antibody-small molecule conjugates are prepared by linking the DOX derivative maleimidocaproyl doxorubicin hydrazone or the maleimidocaproylhydrazone of Adriamycin® (doxorubicin) to E19, E26 or control immunoglobulin following the procedure of Hellstrom, U.S. Pat. No. 5,980, 896. Antibody is diluted with 0.0095 M PBS to a protein concentration of 10.49 mg/mL. This solution (500 mL) is heated to 37° C., under a nitrogen atmosphere, in a water bath. Dithiothreitol (26.2 mL, 10 mM) in PBS is added and the solution is stirred for 3 hrs at 37° C. The solution is divided equally between two Amicon Model 8400 stirred ultrafiltration cells each fitted with a YM 30 ultrafilter (MW cutoff 30,000, 76 mm diam.) and connected via a Model CDS10 concentration/dialysis selector to a Model RC800 mim-reservoir (Amicon, Division of W. R. Grace and Co., Beverly, Ma.). Each reservoir contains 800 mL of 0.0095 M PBS-0.1 M L-histidine. The protein solutions are dialyzed until the concentration of free thiol in the filtrate was 63 .mu.M. The molar ratio of—SH/protein in the retentate is determined to be 8.16. The retentate is transferred from the cells to a sterile container under nitrogen and a solution of maleimidocaproyl hydrazone of Adriamycin® (doxorubicin) (42.6 mL, 5 mg/mL in water) is added with stirring. The conjugate is incubated at 4° C. for 48 hrs after which it is filtered through a 0.22.mu. cellulose acetate membrane. A 2.5 cm.x.50 cm Bio-Rad Econocolumn is packed with a slurry of 100 g of BioBeads.TM.SM-2 (Bio-Rad Laboratories, Richmond Calif. 94804) in 0.0095 M-0.1 M L-histidine buffer. The beads are prepared by washing in methanol, followed by water then several volumes of buffer. The filtered conjugate is percolated through this column at 2 mL/min. After chromatography the conjugate is filtered through a 0.22.mu. cellulose acetate membrane, frozen in liquid nitrogen and stored at −80° C. The conjugate obtained has a molar ratio of 6.77 Adriamycin® (doxorubicin) to protein and is obtained in 80–95% yield.

Example 13

Biological Activity of conjugates.

Representative conjugates of the present invention are tested in both in vitro and in vivo systems to determine biological activity. The potency of conjugates of cytotoxic drugs is determined by measuring the cytotoxicity of the conjugates against cells of human cancer origin. The following describe representative tests and results. The conjugates are referred to using the form ligand-drug-molar ratio of ligand to drug.

Experimental Human Angiogenesis Assay.

The assay system measures human angiogenesis, invasion and metastasis in the chimeric mouse:human model and is referred to as the experimental human angiogenesis assay. The assay has been described in detail by others, and further has been described herein to measure human angiogenesis, invasion and metastasis. See (Yan et al., 1993). Yan, et al., J. Clin. Invest., 91:986–996 (1993).

The experimental human angiogenesis assay is a useful assay model for in vivo angiogenesis because the transplanted skin grafts closely resemble normal human skin histologically. In this model, human cancer cell invasion and neovascularization are occurring wherein actual human blood vessels and tissue are growing from the grafted human skin into the human tumor tissue on the surface of the grafted human skin. The origin of the neovascularization into the human graft can be demonstrated by immunohistochemical staining of the neovasculature with human-specific endothelial cell markers. The invasion and metastasis of human cancer cells may be monitored also.

As demonstrated herein, the experimental human angiogenesis assay demonstrates regression of neovascularization based on both the amount and extent of regression of new vessel growth. Furthermore, effects on the invasion and metastasis of any cancer tissue transplanted upon the grafted skin are easily monitored. Finally, the assay is useful because there is an internal control for toxicity in the assay system. The SCID mouse is exposed to any test reagent, and therefore the health of the mouse is an indication of toxicity.

The experimental human angiogenesis model is prepared essentially as described in Yan, et al., J. Clin. Invest., 91:986–996 (1993). Briefly, a 2 cm$^2$ square area of skin is surgically removed from a SCID mouse (6–8 weeks of age) and replaced with a human foreskin. The mouse is anesthetized and the hair removed from a 5 cm$^2$ area on each side of the lateral abdominal region by shaving. Two circular graft beds of 2 cm$^2$ are prepared by removing the full thickness of skin down to the fascia. Full thickness human skin grafts of the same size derived from human neonatal foreskin are placed onto the wound beds and held in place with 5-0 monofilament suture (Dermalon®, Davis and Geck Inc., Danbury, Conn.). The graft is covered with a Band-Aid® (bandage), which is sutured to the skin. Micropore surgical tape (3M, St. Paul, Minn.) is also applied to cover the wound. Mice are housed in individual cages.

The LOX human melanoma cell line that expresses only seprase (Fodstad et al., 1988) or MDA-MB-436 breast carcinoma cell line that expresses the seprase-DPPIV complex (ATCC HTB 130), as determined by immunoreactivity of the cells with mAb D28 (anti-seprase) and E3 (anti-DPPIV), are used to form the solid human tumors on the human skin grafts on the SCID mice. A single cell suspension of 5×10$^5$ LOX or MDA-MB-436 cells is injected intradermally into the human skin graft. The mice are then observed for 2 to 4 weeks to allow growth of measurable human tumors.

Following the growth of measurable tumors, SCID mice, which had been injected with LOX or MDA-MB-436 human tumor cells, are injected intravenously into the tail vein with 250 .u.g of either the mAb E19/26 (anti-complex, inhibitory) or E3 (anti-DPPIV, non-inhibitory) twice a week for 2 to 3 weeks. After this time, the tumors are resected from the skin and trimmed free of surrounding tissue. Several mice are evaluated for each treatment with the average tumor weight from each treatment being calculated.

Exposure of the LOX- or MDA-MB-436-seprase complex positive human carcinoma tumor mass in the experimental human angiogenesis model to E19 or E26 (against the active site) causes the decrease from the non-inhibitory mAb E3 treated average tumor weight reduction of 100 mg. Representative examples of LOX tumors treated with the mAb E19 and E3 are examined morphologically. The E3-treated tumors remain large (8 to 10 mm in diameter) and well vascularized whereas those treated with mAb E19 (against the active site) are much smaller (3 to 4 mm in diameter) and lack detectable blood vessels. Thus, the blocking of the seprase-DPPIV complex by the intravenous application of active site-specific E19 or E26 antibodies results in a regression of a human melanoma or carcinoma in this model system.

The foregoing results demonstrate that the membrane-bound serine protease DPPIV and possibly also seprase, play a key role in endothelial migration and sprouting but not capillary stability. In addition, the findings that seprase/DPPIV is expressed specifically at sites of capillary sprouts, and that antibodies to DPPIV inhibited endothelial cell migration and capillary sprouting in various extracellular matrices, without perturbing preexisting capillaries, are consistent with the functioning of these proteases in angiogenesis.

Furthermore, DPPIV has been shown to be a gelatinase (Bermpohl et al., 1998) as well as an adhesion receptor for collagen (Bauvois, 1988; Hanski et al., 1988; Loster et al., 1995) or fibronectin (Cheng et al., 1998; Piazza et al., 1989; Johnson et al., 1993); whereas seprase, originally identified as a 170 kDa membrane-bound gelatinase, also associates with the adhesion receptor α3β1-integrin (Aoyama and Chen, 1990; Mueller et al., 1999). Thus, seprase and DPPIV are specific targets for capillary sprouting.

Example 14

Monoclonal Antibodies:

The rat monoclonal antibodies (mAbs) E26, E19, E3 and F4 are directed against human placental DPPIV according to the method of production of rat mAbs D8 and D28 against human placental seprase as described previously (Pineiro-Sanchez et al., 1997; Goldstein et al., 1997). The seprase-DPPIV complex had been isolated from human placenta, and antibodies were produced as described (Pineiro-Sanchez et al., 1997). Monoclonal antibodies E26, E19, E3 and F4 react with DPPIV of the seprase-DPPIV complex, and are not immunoreactive with the seprase subunit or with serine integral membrane proteinases (SIMPs).

Example 15

Cancer Cell Lines with Altered Levels of DPPIV or Seprase.

The LOX human melanoma cell line (Fodstad et al., 1988) or MDA-MB-436 breast carcinoma cell line (ATCC HTB 130) that express seprase and the seprase-DPPIV complex, respectively, as determined by, immunoreactivity of the cells with mAb D28 (anti-seprase) and E3 (anti-DPPIV), were used to study the role of DPPIV and seprase. For this project, the specific importance of DPPIV and the DPPIV-seprase complex against the MT1-MMP background in cancer invasion and angiogenesis were defined using over-expression of DPPIV in low expresser MDA-MB-231 cells (seprase–/DPPIV–/MT1-MMP+) or LOX malignant melanoma cells (seprase+/DPPIV–/MT1-MMP+), alternatively, anti-sense and ribozyme knockout of mRNA in high expresser MDA-MB-436 (seprase+/DPPIV+/MT1-MMP+) as shown in FIG. 7. Inhibition of protease activity by monoclonal antibodies was related to these cell transfection results.

The characterization of protease expression has been completed in selected human breast carcinoma and melanoma cell lines as well as in a pilot study using 70 cases of invasive ductal carcinoma and their respective, adjacent "normal" tissues. RT-PCR was used to investigate the presence of mRNA, Western blotting for relative protein expression levels, gelatin zymography and Ala-Pro-AMC substrate overlay assay for seprase and DPPIV enzymatic activities, respectively, immunofluorescence for surface localization at invadopodia, and immunohistochemistry (IHC) for cell type-distribution of seprase and DPPIV, as well as endothelial and epithelial marker stainings. In summary, the involvement of seprase, DPPIV and MT1-MMP was found at invadopodia. However, two moderately invasive human breast carcinoma cell lines were identified: a seprase and DPPIV low expresser MDA-MB-231 (seprase–/DPPIV–/MT1-MMP+) and a seprase and DPPIV high expresser MDA-MB-436 (seprase+/DPPIV+/MT1-MMP+) as shown in FIG. 7. These two cell lines offer an opportunity to examine relative contribution of seprase and DPPIV, against the background of MT1-MMP in cell invasiveness.

Figure 8A:
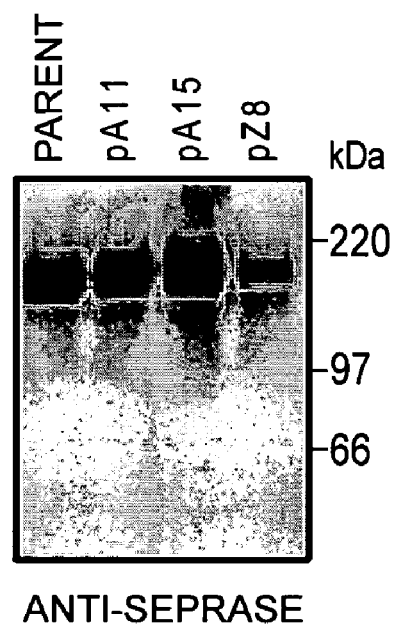
FIG. 8. Protein expression and inhibition of collagen degradation of MDA-MB-436 cells transfected with seprase sense (pA15), seprase anti-sense (pA26), plasmid (pA11), and DPPIV ribozyme (Rbz8) constructs. Cell lysates of stable transfectants of the MDA-MB-436 parent line, which has integrated various construct expression vector (pCR3.1) were analyzed by Western blotting using antibodies against seprase and DPPIV. Rbz 8 blocks DPPIV protein expression in MDA-MB-436 cells. Cells transfected with antisense seprase (p26) or DPPIV ribozyme (Rbz8) show a partial inhibition of collagen-degrading activities. TRITC collagen peptide release is shown as ng per ml medium.
Figure 8B:
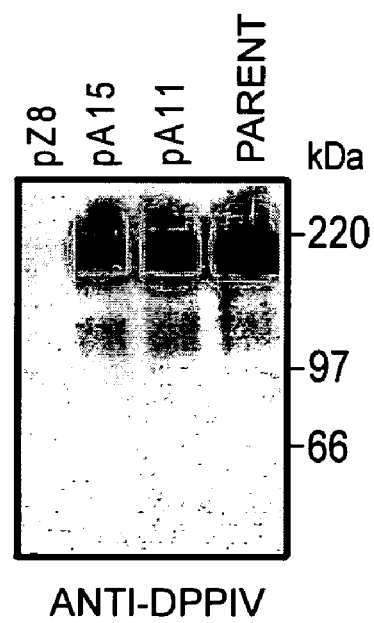
Figure 8C:
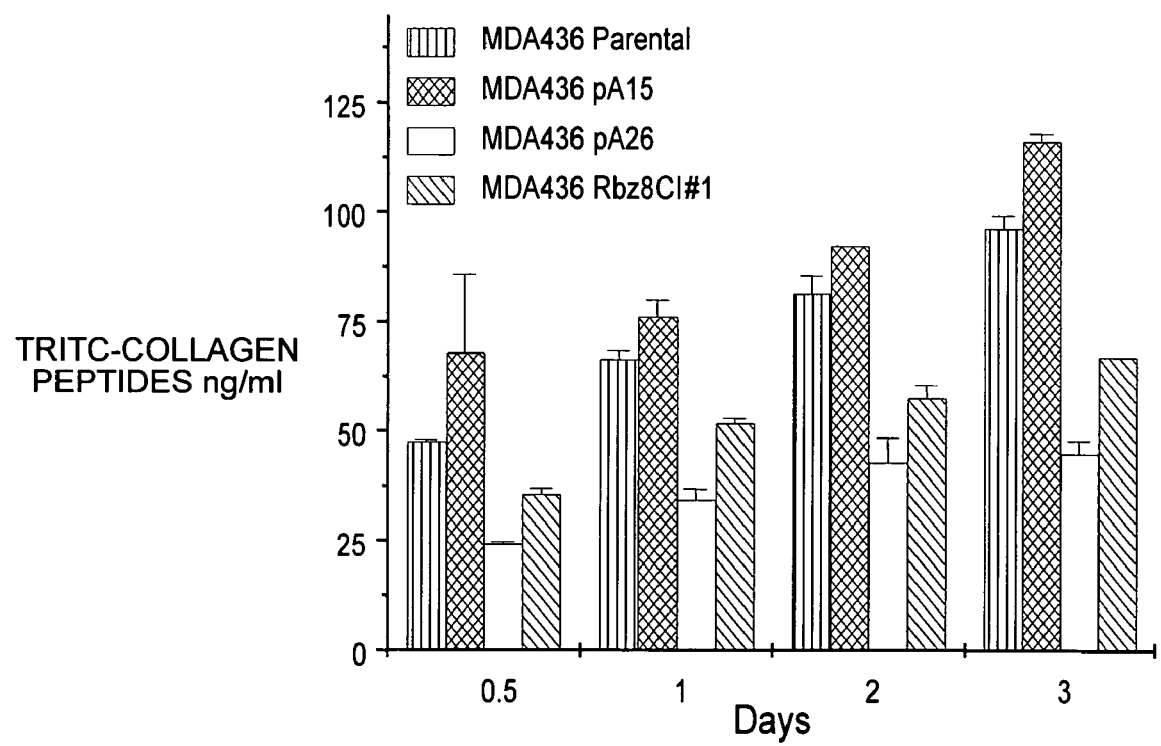

Studies abrogating seprase or DPPIV expression in invasive cells that expressed these proteases constitutively by antisense and ribozyme constructs have been performed. Initially, anti-sense and ribozyme methods were applied to the moderately invasive breast carcinoma cell line, MDA-MB-436 (seprase+/DPPIV+/MT1-MMP+). A stable transfectant of the MDA-MB-436 parent line has been isolated, which has integrated a recombinant expression vector (pCR3.1) containing seprase cDNA in the antisense orientation into its genome (pA26). The cells suppress the seprase expression. The ability of the cells to degrade collagen fiber is partially reduced (FIG. 8). A ribozyme construct (rbz8C#1) according to the method of ribozyme knockout of mRNA (Haseloff and Gerlach, 1988) has been assembled. The ribozyme exhibits in vitro cleavage activity against a DPPIV transcript at the selected site. FIG. 8 shows that the ribozyme blocks not only DPPIV but also seprase protein expression in MDA-MB-436 cells as demonstrated by Western blotting. The stable MDA-MB-436 cell line that had DPPIV RNA-ribozyme knockout partially blocked the degradation of collagen matrix by the cells. It was surprising that the DPPIV-ribozyme cells also suppressed seprase expression (FIG. 8). Furthermore, the degradation of collagen matrix by this cell line was only observed being moderate (FIG. 8), suggesting that a complicated process of regulation may occur in this protease expression system.

Using the ribozyme approach, DPPIV expression was abrogated in invasive cells to examine the influence of individual membrane proteases on tumor cell proliferation and invasiveness. A hammerhead ribozyme usually consists of a catalytic center made up of a highly conserved sequence of 22 nucleotides and two flanking regions that base-pair the ribozyme with targeted RNA sequences flanking the trinucleotide GUX, where X can be A, C or U. A ribozyme normally cleaves on the 3' side of the trinucleotide in the targeted RNA (Haseloff and Gerlach, 1988). To generate ribozyme constructs targeted at DPPIV, the cDNA sequence was scanned and potential cleavage sites identified. A pair of sense and anti-sense oligonucleotides with complimentary 3' ends, covering the sequences of the catalytic center and flanking regions of the cleavage site have been synthesized. As an example, the nucleotide sequences of sense and antisense oligonucleotides used to construct the ribozyme #8 (rbz#8) targeting a site in the seprase sequence are shown as follows:

```
5'-AGGCACTGAACTGATGAGTCCGTGAGG-3'   (SEQ. ID. NO: 3)
Sense oligonucleotide

5'-TGAAGAGGAAGTTTCGTCCTCACGG-3'    (SEQ. ID. NO: 4)
Antisense oligonucleotide
```

Example 16

Characterization of the DPPIV Catalytic Site: (a) Enzymatic Assays for the DPPIV Catalytic Site.

A commercial chromogen, Gly-Pro-p-nitroanilide (pNA), is a substrate for the catalytic domains of both DPPIV and the seprase-DPPIV complex. Inhibitors of DPPIV include compounds containing phosphorylated residues adjacent to proline, e.g., H-Ile-Pro-NHO-pNB, an irreversible suicide DPPIV inhibitor; H-Ile-Thia, a reversible DPPIV inhibitor (Ki=8×10−8); and H-Glu(Gly5)-Thia, a reversible DPPIV inhibitor (Ki=8×10−8) (Kaspari et al., 1996), which blocks DPPIV catalytic activity against Gly-Pro-pNA. The effect of various mAbs against DPPIV (E3, F4, E19 and E26) on the catalytic activity was examined. However, none of these antibodies block DPPIV dipeptidase activity against Gly-Pro-pNA. Interestingly, the mAbs E19 and E26 enhance DPPIV dipeptidase activity against Gly-Pro-pNA 3–5 folds but mAbs E3 and F4 do not. Thus, E19 and E26 antibodies do not have inhibitory activity against the catalytic sites as assayed by these small peptide substrates. However, binding of mAbs E19 and E26 to DPPIV may modify the proteolytic activity of the enzyme.

(b) Antibody inhibition of DPPIV substrate sites that bind to type I collagen.

Figure 9A:
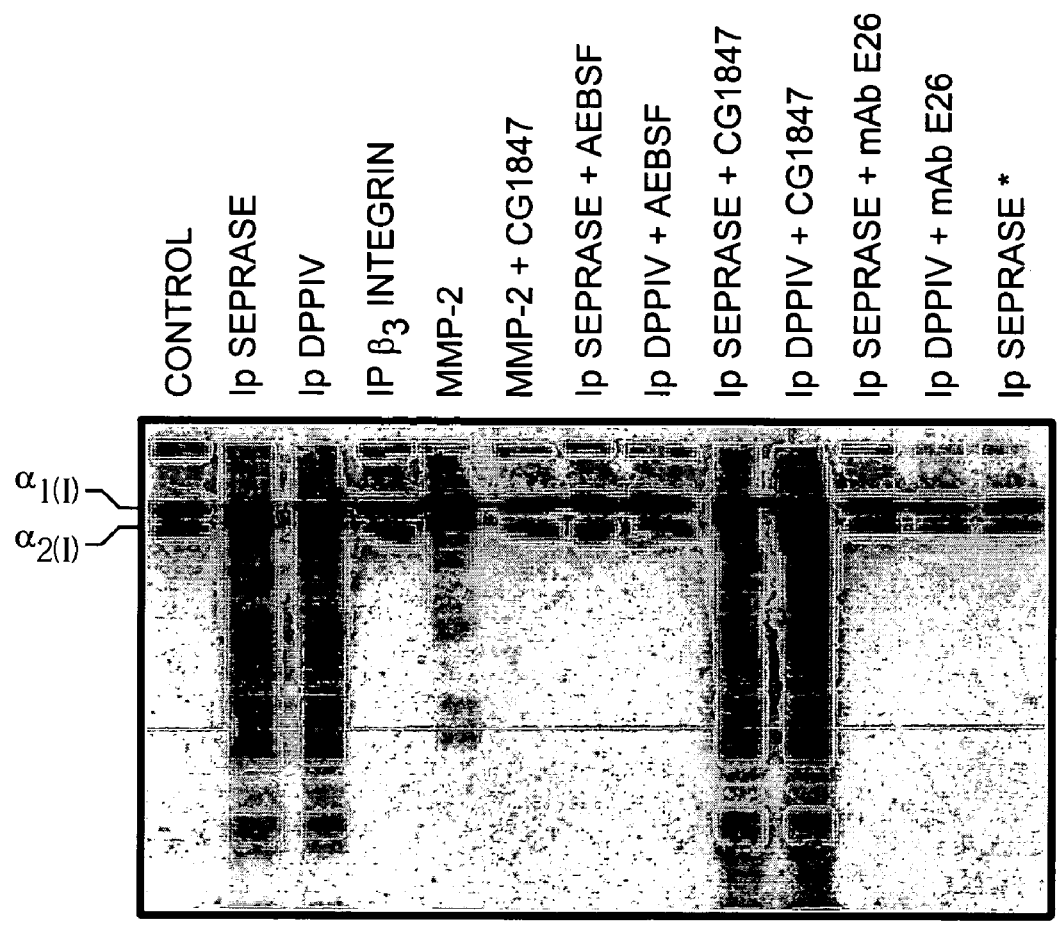
FIG. 9. Collagen-degrading activity of the seprase-DPPIV complex. Collagen-degrading activities of the protease complex and purified DPPIV were determined by the release of peptide fragments from biotinylated type I collagen gel in the presence of these enzymes. The seprase-DPPIV complex was isolated from WI38 RIPA extracts using mAbs D28 (lane marked Ip Seprase) and E3 (lane marked Ip DPPIV) beads, seprase from LOX WGA fraction using mAb D28 (lane marked Ip Seprase*), MMP-2 from media conditioned by MMP-2 COS cell transfectants (lane marked MMP-2), and proteins associated with β3 integrin were from WI38 RIPA extracts using HB242 (lane marked Ip β3 integrin). All enzymes, including the protease complex, purified seprase, MMP-2, and proteins associated with β1 or β3 integrin were applied at the concentration of 50 ng/ml. Biotinylated type I collagen and enzymes were incubated for 8 h at 37° C. with proteins described above, plus the mAb C37 control (5 μg/ml, lane marked Control) or inhibitory anti-DPPIV mAb E26 (5 μg/ml, lanes marked +E26), the serine-proteinase inhibitor AEBSF (20 μM, lanes marked +AEBSF), and the metallo-proteinase inhibitor CG1847 (50 nM, lanes marked +CG1847). Profiles of collagen peptide release (shown in panels at right of the figure) were scanned with a densitometer. The seprase-DPPIV complex degrades collagen fibers to produce a novel multiple-peptide pattern.
Figure 9B:
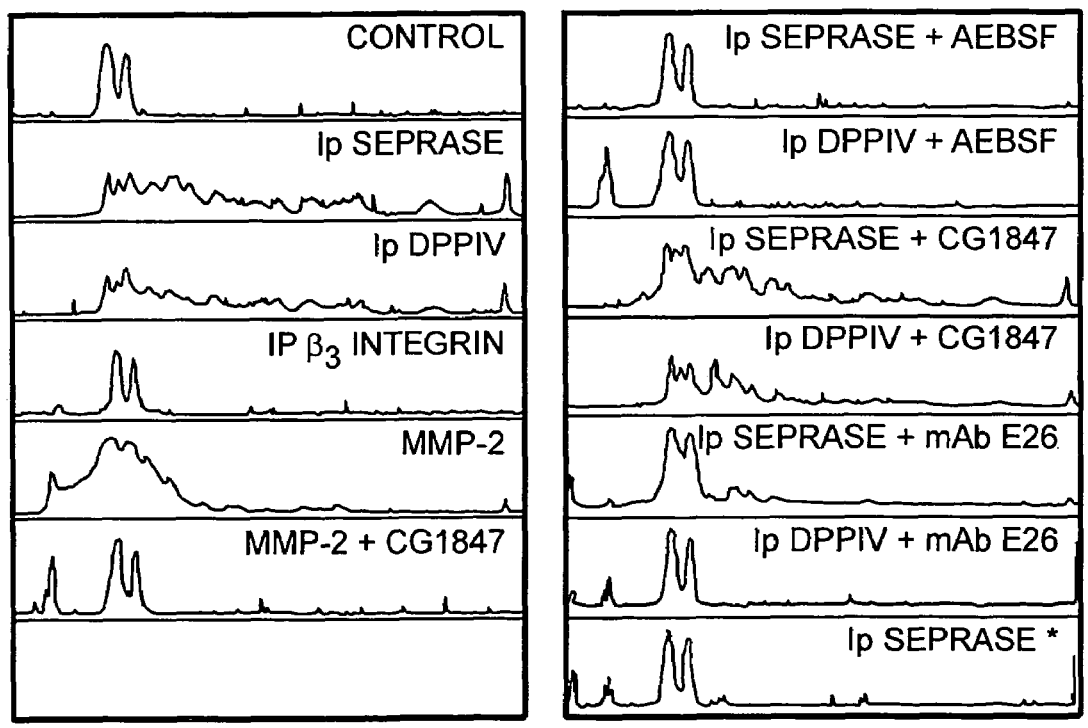

Collagen-degrading activity of isolated DPPIV or seprase-DPPIV complex was determined by the release of peptide fragments from biotinylated type I collagen gel by immuno-isolated proteases or the protease complex. FIG. 9 shows the peptides released from the collagen gel in the presence of DPPIV or protease complex and potential inhibitors. The reaction was performed at 37° C. for 8 h, during which time collagen gels in protein controls (FIG. 9, lanes marked Control and Ip β3 integrin) remained in gel form and relatively intact. However, when the reaction was performed at 37° C. for 8–24 h, properties of denatured collagen were seen, i.e., auto-released collagenous peptides with more accessibility to MMP-2 digestion (FIG. 9). This confirms that the degradation of collagen by the seprase-DPPIV complex is due to gelatinolytic activity of the enzymes. The seprase-DPPIV complex, immuno-isolated by anti-seprase or DPPIV antibodies, exhibited a gelatinolytic activity that released multiple peptide fragments from the collagen gel, which differed from that by MMP-2 (FIG. 9). The collagen peptide pattern generated by the seprase-DPPIV complex appears to be due to a close cooperation between seprase and DPPIV in the protease complex, and the degradation is blocked by inhibitory mAbs E19 and E26 and the serine-proteinase inhibitor AEBSF, but not by the metallo-proteinase inhibitor CG1847 (FIG. 8). In addition, uncomplexed seprase derived from LOX melanoma cells and uncomplexed DPPIV isolated from bovine kidney brush border membranes did not show such collagen degrading activity. Thus, the DPPIV-seprase complex exhibits an extensive gelatin-degrading activity, and E19 and E26 inhibition of the degradation may result from antibody effects on binding of collagen substrates to the enzymes.

To map epitopes recognized by mAbs E19 and E26 at substrate binding sites for type I collagen, a competition assay was performed. A 96-well microtiter plate was coated with rat anti-DPPIV mAbs E3 or F4 and incubated at 37° C. for 2 hours. The cell lysates containing the seprase-DPPIV complex, recombinant seprase or DPPIV were added and incubated at 37° C. for 2 hours. Biotinylated type I collagen, 5 μg/ml, was added in the presence of various concentrations, from 0.1 to 50 μg/ml, of mAbs E19, E26, E3 or F4.

Following incubation and washing, Alkaline Phosphatase (AP) conjugated streptavidin was added to wells, and the reaction was detected by adding AP substrate (p-nitrophenylphosphate) and reading the absorbance at 405 nm. E19 and E26 antibodies but not E3 and F4 antibodies recognize specific sites on DPPIV and the DPPIV-seprase complex that bind to type I collagen.

The possibility that DPPIV functions as an adhesin receptor was examined by investigating the inhibitory effect of mAbs E19 or E26 (against DPPIV) as compared to that of mAb C27 (against β1 integrins) on cellular attachment and spreading on a collagen substratum. In a parallel comparison to integrin adhesion to collagen fibers, while mAbs E19 or E26 (against DPPIV) inhibit cellular migration in collagen gels and collagen degradation by migratory cells (see below) these mAbs do not affect cellular spreading and attachment on a collagen substratum. However, mAb C27 inhibits cellular spreading on and adhesion to collagen substratum but mAbs E19 or E26 do not. These data demonstrate that whereas β1 integrins may be the primary collagen receptors on the cells responsible for cellular adhesion and spreading, DPPIV binding to collagen substrate is involved in the modification of collagenous matrices and subsequent cellular invasion.

Example 17

Characterization of Tissue Distribution of Seprase-DPPIV Complex Expression.

Based on immunohistochemistry (IHC) and seprase-specific gelatin zymography, seprase/FAPα expression was found to be high in mesenchymal and endothelial cells of placental tissues (Pineiro-Sanchez et al., 1997) but undetectable in human adult skin, mammary gland, gingival mucosa, and other connective tissues. Based upon mAb F19 reactivity, FAPα was originally proposed as a specific marker for "activated" fibroblasts as it was found to be expressed on reactive stromal fibroblasts of epithelial cancers and healing wounds but not in all adult tissue cells, particularly epithelial and endothelial cells (Garin-Chesa et al., 1990). Consistent with putative FAPα function in wound repair, seprase was found to be expressed transiently in mucosa cells within 1–3 days after gingival surgery. However, IHC studies for seprase expression and biochemical analysis for its function have not been done in other normal tissues and blood-borne cells, the expression and function of seprase/FAPα in normal tissue remains to be determined.

DPPIV expressions are also high in embryonic tissues and some adult tissues, including small intestine, lung and kidney. DPPIV, in specialized epithelial cells, is expressed constitutively on brush border membranes of epithelial cells of intestine and kidney, as well as the apical surface of some specialized epithelial cells, i.e., bile canaliculi of hepatocytes (Yaron and Naider, 1993; Morimoto and Schlossman, 1994). However, its transient expression on T-cells has been implicated as a marker for T-cell activation (Morimoto and Schlossman, 1994; Vivier et al., 1991). Similar to seprase, IHC studies and biochemical analysis for DPPIV function have not been done in other normal tissues and blood-borne cells, its expression and function in normal tissue remains to be determined.

To investigate the expression of the seprase-DPPIV complex during cancer invasion, angiogenesis and tissue repair, human wound granulation tissue or adjacent normal skin and infiltrating ductal carcinomas or their corresponding adjacent normal tissues were examined. Human gingival biopsies were derived from the University of Turku, Finland. Full thickness wounds of oral mucosa were made from two healthy volunteers and biopsies were collected after 3, 7, 14 and 28 days of wounding. Immediately after biopsy, fresh tissue blocks were mounted in Histoprep® (Fisher Scientific, New Jersey) and snap frozen in liquid nitrogen. Frozen sections (6 μm) were cut, fixed with acetone at −20° C. for 5 min, and stored at −70° C. For routine histology, the sections were stained with hematoxylin and eosin. For immunohistochemical staining, sections were washed with PBS containing 0.1% bovine serum albumin (BSA; Sigma Chemical Co., St. Louis, Mo.) and incubated with rhodamine-conjugated mAb D28 against seprase or mAb E19 against DPPIV in PBS/BSA in humid chamber at 4° C. for 16 h. The sections were then washed with PBS/BSA and water, briefly air-dried, and mounted using cyanoacrylate glue (Krazy Glue®, Borden Company LTD). The staining was examined using a Zeiss Axioskop 20 light, fluorescence and confocal microscopy, and photographed using MC 80 Zeiss microscope camera. Control staining was performed with rhodamine-conjugated secondary antibody and showed no specific stain. Immunohistochemical staining of invasive human breast carcinoma was performed as described (Kelly et al., 1998).

Unlike human umbilical cord smooth muscle cells in culture (Goldstein et al., 1997), both seprase and DPPIV preferentially distribute among mesenchymal cells but not differentiated muscle and endothelial cells of large vessels in human embryonic tissues, including placenta and umbilical cord. To determine if seprase and DPPIV expression in stromal fibroblasts is induced during wound closure in vivo, the immunohistochemistry of human gingival mucosa-wound closure was investigated. A strong expression of seprase and DPPIV was seen in connective tissue cells at day 3 after wounding. Later, at day 7 after wounding, only a few cells in the middle of granulation tissue were reactive with the anti-seprase antibody but not the anti-DPPIV antibody. Seprase and DPPIV staining disappeared from connective tissue cells after one week and cells of normal mucosa adjacent to wounds also did not react with the antibodies against seprase and DPPIV. Furthermore, no specific reaction was seen in the fibrin clot area and epithelium. Seprase and DPPIV appear to be activation enzymes on fibroblastic cells that participate in the local degradation of connective tissue necessary for cellular migration.

Immunohistochemistry of human breast invasive carcinoma and adjacent normal tissue: The immunohistochemistry procedure involves fixation of invasive breast cancer and adjacent tissues with 4% paraformaldehyde in PBS for 2–4 h at 4° C., followed by paraffin embedding. Paraffin-embedded tissue blocks were sectioned in 4-μm-thick pieces using a microtome. The samples were adhered to glass slides (Matsunami, Tokyo, Japan) and dried at 42° C. overnight. The slides were cooled and de-paraffinized through three changes of Americlear® (histology cleaning solution) (Baxter, Deerfield, Ill.). Then the slides were rinsed in 100% ethanol twice and 95% ethanol twice and re-hydrated with distilled water. Antigens were retrieved by treating slides in a container covered with 10 mM sodium citrate buffer, pH6.0, and heated at 120° C. for 5 mm by autoclave. After heat treatment, the buffer was allowed to cool down to normal temperature, and replaced with PBS. The slides were then treated with 10% normal blocking serum in PBS for 15–30 min. Blocking serum should be derived from the species in which the secondary antibody was made: normal horse serum was used for primary mouse monoclonals, and normal rabbit serum for primary rat monoclonals. Anti-seprase mAbs D8 or D28 or anti-DPPIV mAbs E19 or E26 in serum-free supernatant form were added at a dilution of 1:10 to 1:25 to each tissue section and incubated at 4° C. overnight in a humidity chamber. Mouse mAb against human endothelial cells (CD34, Cosmo Bio Co. Ltd., Tokyo, Japan) were added at a dilution of 1:50; and a mixture of three mouse mAbs, including C11 (1:400), ESA (1:50) and EMA (1:60) were used for marking epithelial cells. Bound primary antibody was then detected by streptavidin-biotin-peroxidase technique (DAKO) according to the manufacturer's instructions using diaminobenzidine (3,3'-diaminobenzidine tetrahydrochloride, Sigma, St. Louis, Mo.) as a chromogen and counter-staining was performed with hematoxylin.

Co-localization of seprase and DPPIV was seen in microvessel endothelial-epithelial cells at the invasion front of human malignant breast ductal carcinoma. Human malignant breast ductal carcinomas were formaldehyde-fixed and paraffin embedded. Serial sections were stained with rat mAb D8 or D28 directed against seprase (labeled as Sep); rat mAb E26 or E19 directed against DPPIV (DPP4); mouse mAb against endothelial marker antigen CD34 or CD31 (Endo); or mouse mAbs against epithelial marker antigens C11, ESA and EMA (Epi). Open arrowheads indicate sites of micro-vessels located in the front of infiltrating sheets of poorly differentiated (high-grade) carcinoma that are identified as a putative "angiogenic center". In the center, the vessel lining cells were stained positively with seprase, DPPIV, endothelial and epithelial markers, and they are referred as "metastatic cells". Arrows indicate the carcinoma cells in tumor, and also a scale of 50 µm. Note that, in adjacent areas, seprase and DPPIV are differentially expressed in carcinoma and endothelial cells.

Distribution of seprase and DPPIV in mammary glands adjacent to their respective malignant breast ductal carcinoma tumors was assayed immunohistochemically. The tissues adjacent to malignant breast ductal carcinomas were formaldehyde-fixed and paraffin embedded side-by-side with the tumors. Serial sections were stained with rat mAb D8 or D28 directed against seprase; rat mAb E26 or E19 directed against DPPIV; mouse mAb against endothelial marker antigen CD34 or CD31; or mouse mAbs against epithelial marker antigens C11, ESA and EMA. Sites of micro-vessels were located surrounding the mammary glands. In most areas, seprase and DPPIV were not detectable in all cell types, except that low levels of DPPIV were detected in a few mammary glands using high titer of primary antibodies, 10 µg/ml. Some background brown staining was seen on connective tissue fibers due to the high titer of the antibodies used.

As described above, protease expression was characterized in selected human breast carcinoma cell lines as well as in an immunohistochemistry (IHC) study using 70 cases of invasive ductal carcinoma and their respective, adjacent "normal" tissues. Seprase and DPPIV are expressed in a subset of carcinoma cells at the invasion front of tumor and in a subset of carcinoma cells at sites of putative "angiogenic center", but not other tumor cells and not in most epithelial and endothelial cells in adjacent tumor tissue. An intense but limited protease expression pattern was observed at putative "angiogenic sites" in the invasion front of tumors. At these sites, the carcinoma cells with large nuclei line the microvessel, express both seprase/DPPIV and epithelial/endothelial marker antigens, suggesting that these cells are of carcinoma origin and are invasive (based on their expression of seprase and DPPIV). However, both epithelial and endothelial cells in normal tissues adjacent to their respective tumors did not express seprase and DPPIV, except a subset of mammary epithelial cells had weak DPPIV staining.

These results described herein show that DPPIV of the seprase-DPPIV complex is selectively expressed in specific tissue types, namely granulated, metastatic tissues and other tissues in which angiogenesis and cell invasion are occurring and not normal tissue where the formation of new blood vessels and cell invasion have stopped. These tissues therefore provide an ideal target for therapeutic methods according to the present invention.

Example 18

Suppression of Cancer Invasion and Metastasis with DPPIV Antagonists as Measured by In Vivo Experimental Models.

Monoclonal antibodies E19 and E26 that show positive effects in cell invasion and angiogenesis assays in culture were assessed for their in vivo activity using an experimental human invasion/metastasis model (Thompson et al., 1992). Human breast carcinoma cell line MDA-MB-436 (seprase+/DPPIV+) and human malignant melanoma cell line LOX (seprase+/DPPIV−) were used as a basis for these animal studies. Seprase+/DPPIV+and seprase+/DPPIV− cells were transformed with a retrovirus vector for lacZ tag as described (Kern et al., 1994) and these cells, $0.5 \times 10^6$, were subcutaneously injected into 6-8 week-old female athymic (nu/nu) mice. Antibodies or inhibitors were subcutaneously co-inoculated orthotopically with human cancer cells (seprase+/DPPIV+ and seprase+/DPPIV−), followed by intravenous injection into the tail vein with 250 µg of the mAb E19, E26, or E3 (anti-DPPIV) twice a week for 2 to 3 weeks, to examine their effects on tumor invasion and tissue colonization as described (Kern et al., 1994). Injected mice were examined twice weekly for tumor sizes. Mice were maintained for 2–3 months or until primary tumor reaching 2 cm in diameter, after which the primary tumor and selected organs (lung and liver) were assayed for β-galactosidase activity, histological analysis and immunohistochemical localization of endothelial cell type markers, seprase and DPPIV. Antibodies and inhibitors for MMPs, such as TIMP-2 or synthetic compounds CT1817 and Marinmastat AG3340, as a positive inhibitory control for MMP effect, were used to test for the function of membrane proteases in vivo.

Tumors formed in nude mouse skin, which had been injected with human cancer cells (seprase+/DPPIV+ and seprase+/DPPIV−) were detectable and measureable. Morphological examination of the established tumors and lung metastases revealed that invasion and metastasis of human cancer cells into mouse tissue had occurred. The invasion and metastasis of human carcinoma cells were determined by the localization of blue-stained β-galactosidase tagged cancer cells and immunohistochemical staining using human-specific epithelial cell markers, including anti-human Muc-1 and epithelial surface antigen antibodies that were conjugated with a marker biotin. In addition, the blocking of the DPPIV by the intravenous application of DPPIV-specific E19 or E26 monoclonal antibodies resulted in a slowing of cancer invasion and lung metastasis in this model system.

Example 18

In vivo Regression of Human Tumor Growth and Angiogenesis with DPPIV Antagonists as Measured by a Chimeric Mouse-Human Assay.

The effects of monoclonal antibodies on human tumor growth and angiogenesis were assessed by co-inoculating human breast carcinoma cell line MDA-MB-436 (seprase+/

DPPIV+) or human malignant melanoma cell line LOX (seprase+/DPPIV−) or ovarian cancer cells (seprase+/DPPIV+) with endothelial cells (CD31+) isolated from ovarian cancer ascites into the skin of SCID or nude mice. Severe combined immunodeficiency (SCID) mice, C.B-17-scid strain, were used in this assay. SCID lack both T and B cells due to a defect in V(D)J recombination, and SCID mice do not mount an antibody response to challenge by immunogenic material. Therefore, they easily accept foreign tissue transplants, including human cells. The SCID-human model was prepared essentially as described in (Yan et al., 1993). Briefly, seprase+/DPPJV+ and seprase+/DPPIV− cells tagged with lacZ were mixed with CD31+human endothelial cells in Matrigel® (basement membrane matrix) ($2 \times 10^6$ cells each cell type), in the presence of monoclonal antibodies or inhibitors, were subcutaneously injected into 6–8 week-old SCID mice. Mice were housed in individual cages. The mice were then observed for 2 to 4 weeks to allow growth of measurable human tumors. Following the growth of measurable tumors, SCID mice were injected intravenously into the tail vein with 250 µg of either the mAb E19, E29 or E3 (anti-DPPIV) twice a week for 2 to 3 weeks. After this time, the tumors were resected from the skin and trimmed free of surrounding tissue. Three to four mice were used for each treatment and the result of suppression of tumor growth (as determined by size) with DPPIV antagonist antibodies are shown in Table I. The color of the tumor and immunohistochemistry results were used to indicate the degree of tumor angiogenesis. In this model, human tumor growth and neovascularization were occurring in the mouse tissue. The cell origin of the neovascularization within the human tumor was demonstrated by immunohistochemical staining of the neovasculature with human-specific endothelial cell markers, including anti-human factor VIII and CD31 antibodies.

TABLE I

| MDA-MB-436 Tumor Number | Treatment | Tumor Weights (mg) | Average Tumor Weights (mg) |
|---|---|---|---|
| 1 | E3/control | 225 | 210 |
| 2 | E3/control | 203 | |
| 3 | E3/control | 179 | |
| 4 | E3/control | 213 | |
| 5 | E19 | 125 | 102 |
| 6 | E19 | 97 | |
| 7 | E19 | 113 | |
| 8 | E19 | 78 | |
| 9 | E26 | 69 | 92 |
| 10 | E26 | 89 | |
| 11 | E26 | 134 | |
| 12 | E26 | 77 | |

Exposure of the human carcinoma tumor mass in the mouse:human chimeric assay system to mabs E19 or E26 (anti-DPPIV antibodies that block cell migration and invasion in culture) caused the decrease from the E3 (a control, non-inhibitory anti-DPPIV antibody) treated average tumor weight of 210 mg to 102 mg and 92 mg, respectively. Representative examples of tumors treated with the mAb E26 (inhibitory anti-DPPIV) and E3 (control anti-DPPIV) were examined morphologically. The E3-treated tumors were large (11 to 14 mm in diameter) and well vascularized whereas those treated with mAb E26 (inhibitory anti-DPPIV) were much smaller (4 to 7 mm in diameter) and lacked detectable blood vessels. Immunohistochemical examination of the established tumors revealed that human neovascularization into the human tumor had occurred in mouse skin. The DPPIV membrane protease was blocked by the intravenous application of inhibitory DPPIV E19 or E26 antibodies resulting in a regression of a human tumor in this model system in the same manner as the experimental invasion and metastasis model systems as described in the Examples above.

A therapeutically effective amount of DPPIV antagonist of this invention in the form of a monoclonal antibody, or fragment thereof, is typically an amount such that when administered in a physiologically tolerable composition is sufficient to achieve a plasma concentration of from about 0.01 microgram (µg) per milliliter (ml) to about 100 µg/ml, preferably from about 1 µg/ml to about 5 µg/ml, and usually about 5 µg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The monoclonal antibodies of the invention can be administered by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies or polypeptides of the invention can be administered intravenously, intraperitoneally, intramuscularly, subcutaneously, intracavity, transdermally, and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluents; i.e., carrier, or vehicle. The compositions are administered in a manner compatible with the dosage formulation, and in a therapeutically effective amount. The quantity to be administered depends on the subject to be treated, capacity of the subject's system to utilize the active ingredient, whether the therapeutic composition is metabolized and/or excreted, and the degree of therapeutic effect desired.

Precise amounts of active ingredient to be administered may be determined by the practitioner by routine methods and are peculiar to each individual. However, suitable dosage ranges for systemic application are disclosed herein and depend on the route of administration. Suitable regimens for administration are also variable, but are typified by an initial dose followed by repeated doses at one or more hourly intervals by a subsequent injection or other routes of administration. Alternatively, continuous intravenous infusion sufficient to maintain concentrations in the blood in the ranges specified for in vivo therapies are contemplated.

As demonstrated by the present Examples, inhibition of angiogenesis and tumor regression occurs as early as 7 days after the initial contacting with antagonist. Additional or prolonged exposure to antagonist is preferable for 7 days to 6 weeks, preferably about 14 to 28 days.

Those of skill in the art will immediately recognize further embodiments of the present invention which are exemplified in the specification and claims herein presented.

REFERENCES

Aoyama, A. and Chen, W.-T. (1990). A 170-kDa membrane-bound protease is associated with the expression of invasiveness by human malignant melanoma cells. Proc. Natl. Acad. Sci. U. S. A. 87, 8296–8300.

Bauvois, B. (1988). A collagen-binding glycoprotein on the surface of mouse fibroblasts is identified as dipeptidyl peptidase IV. Biochem. J. 252, 723–731.

Bermpohl, F., Löster, K., Reutter, W., and Baum, O. (1998). Rat dipeptidyl peptidase IV (DPP IV) exhibits endopeptidase activity with specificity for denatured fibrillar collagens. FEBS Letters 428, 152–156.

Bloch, W., Forsberg, E., Lentini, S., Brakebusch, C., Martin, K., Krell, H. W., Weidle, U. H., Addicks, K., and Fässler, R. (1997). b1-integrin is essential for teratoma growth and angiogenesis. J. Cell Biol. 139, 265–278.

Brooks, P. C., Clark, R. A., and Cheresh, D. A. (1994). Requirement of vascular integrin alpha v beta 3 for angiogenesis. Science 264, 569–571.

Brooks, P. C., Silletti, S., Von Schalscha, T. L., Friedlander, M., and Cheresh, D. A. (1998). Disruption of angiogenesis by PEX, a noncatalytic metalloproteinase fragment with integrin binding activity. Cell 92, 391–400.

Chen, W.-T. (1996). Proteases associated with invadapodia, and their role in degradation of extracellular matrix. Enzyme Protein 49, 59–71.

Chen, W.-T., Lee, C. C., Goldstein, L., Bernier, S., Liu, C. H., Lin, C. Y., Yeh, Y., Monsky, W. L., Kelly, T., Dai, M., and Mueller, S. C. (1994). Membrane proteases as potential diagnostic and therapeutic targets for breast malignancy. Breast Cancer Res. Treat. 31, 217–226.

Chen, W.-T. (1979). Induction of spreading during fibroblast movement. J. Cell Biol 81, 684–691.

Cheng, H. C., Abdel-Ghany, M., Elble, R. C., and Pauli, B. U. (1998). Lung endothelial dipeptidyl peptidase IV promotes adhesion and metastasis of rat breast cancer cells via tumor cell surface-associated fibronectin. J. Biol. Chem. 273, 24207–24215.

Folkman, J. (1995). Seminars in Medicine of the Beth Israel Hospital, Boston. Clinical applications of research on angiogenesis. N. England J. Med. 333, 1757–1763.

Folkman, J. (1990) J. Natl. Cancer Inst. 82:4–6.

Garin-Chesa, P., Old, L. J., and Rettig, W. J. (1990). Cell surface glycoprotein of reactive stromal fibroblasts as a potential antibody target in human epithelial cancers. Proc. Natl. Acad. Sci. USA 87, 7235–7239.

Goldstein, L. A., Ghersi, G., Piñieiro-Sánchez, M. L., Salamone, M., Yeh, Y. Y., Flessate, D., and Chen, W.-T. (1997). Molecular cloning of seprase: A serine integral membrane protease from human melanoma. Biochim. Biophys. Acta Mol. Basis Dis. 1361, 11–19.

Grant, D. S., Kinsella, J. L., Fridman, R., Auerbach, R., Piasecki, B. A., Yamada, Y., Zain, M., and Kleinman, H. K. (1992). Interaction of endothelial cells with a laminin A chain peptide (SIKVAV) in vitro and induction of angiogenic behavior in vivo. J. Cell. Physiol. 153, 614–625.

Hanski, C., Huhle, T., Gossrau, R., and Reutter, W. (1988). Direct evidence for the binding of rat liver DPP IV to collagen in vitro. Exp. Cell Res. 178, 64–72.

Heins J, Welker P, Schonlein C, Born I, Hartrodt B, Neubert K, Tsuru D, Barth A 1988 Mechanism of proline-specific proteinases: (I) Substrate specificity of dipeptidyl peptidase IV from pig kidney and proline-specific endopeptidase from Flavobacterium meningosepticum. *Biochim Biophys Acta* 954(2):161–9.

Hiraoka, N., Allen, E., Apel, I. J., Gyetko, M. R., and Weiss, S. J. (1998). Matrix metalloproteinases regulate neovascularization by acting as pericellular fibrinolysins. Cell 95, 365–377.

Johnson, R. C., Zhu, D., Augustin-Voss, H. G., and Pauli, B. U. (1993). Lung endothelial dipeptidyl peptidase IV is an adhesion molecule for lung-metastatic rat breast and prostate carcinoma cells. J. Cell Biol 121, 1423–1432.

Kelly, T., Kechelava, S., Rozypal, T. L., West, K. W., and Korourian, S. (1998). Seprase, a membrane-bound protease, is overexpressed by invasive ductal carcinoma cells of human breast cancers. Mod. Pathol. 11, 855–863.

Klagsbrunn and Soker, (1993) Current Biology 3:699–702.

Loster, K., Zeilinger, K., Schuppan, D., and Reutter, W. (1995). The cysteine-rich region of dipeptidyl peptidase IV (CD 26) is the collagen-binding site. Biochem. Biophys. Res. Commun. 217, 341–348.

Morimoto, C. and Schlossman, S. F. (1994). CD26: A key costimulatory molecule on CD4 memory T cells. Immunologist 2, 4–7.

Martin, P. (1997). Wound healing—Aiming for perfect skin regeneration. Science 276, 75–81.

Monsky, W. L., Lin, C.-Y., Aoyama, A., Kelly, T., Mueller, S. C., Akiyama, S. K., and Chen, W.-T. (1994). A potential marker protease of invasiveness, seprase, is localized on invadopodia of human malignant melanoma cells. Cancer Res. 54, 5702–5710.

Morimoto C, and Schlossman SF (1994). CD26: A key costimulatory molecule on CD4 memory T cells, Immunologist 2, 4–7.

Mueller, S. C., Ghersi, G., Akiyama, S. K., Sang, Q. X., Howard, L., Pineiro-Sanchez,M., Nakahara, H., Yeh, Y., and Chen, W.-T. (1999). A novel protease-docking function of integrin at invadopodia. J. Biol. Chem. 274, 24947–24952.

Nakahara, H., Howard, L., Thompson, E. W., Sato, H., Seiki, M., Yeh, Y., and Chen, W.-T. (1997). Transmembrane/cytoplasmic domain-mediated membrane type 1-matrix metalloprotease docking to invadopodia is required for cell invasion. Proc. Natl. Acad. Sci. U. S. A. 94, 7959–7964.

Pepper, M. S., Montesano, R., Mandriota, S. J., Orci, L., and Vassalli, J. D. (1996). Angiogenesis: A paradigm for balanced extracellular proteolysis during cell migration and morphogenesis. Enzyme and Protein 49, 138–162.

Pepper, M. S., Sappino, A.-P., Stöcklin, R., Montesano, R., Orci, L., and Vassalli, J.-D. (1993). Upregulation of urokinase receptor expression on migrating endothelial cells. J. Cell Biol. 122, 673–684.

Piazza, G. A., Callanan, H. M., Mowery, J., and Hixson, D. C. (1989). Evidence for a role of dipeptidyl peptidase IV in fibronectin- mediated interactions of hepatocytes with extracellular matrix. Biochem. J. 262, 327–334.

Pineiro-Sanchez, M. L., Goldstein, L. A., Dodt, J., Howard, L., Yeh, Y., Tran, H., Argraves, W. S., and Chen, W.-T. (1997). Identification of the 170-kDa melanoma membrane-bound gelatinase (seprase) as a serine integral membrane protease. J. Biol. Chem. 272, 7595–7601; Correction (1998) J. Biol. Chem. 273, 13366.

Scanlan, M. J., Raj, B. K., Calvo, B., Garin-Chesa, P., Sanz-Moncasi, M. P., Healey, J. H., Old, L. J., and Rettig, W. J. (1994). Molecular cloning of fibroblast activation protein alpha, a member of the serine protease family selectively expressed in stromal fibroblasts of epithelial cancers. Proc. Natl. Acad. Sci. U. S. A. 91, 5657–5661.

Stetler-Stevenson, W. G., Aznavoorian, S., and Liotta, L. A. (1993). Tumor cell interactions with the extracellular matrix during invasion and metastasis. Annu. Rev. Cell Biol. 9, 541–573.

Weidner et al. New England J. of Med. 324:1–8 (1991).

Yaron, A. and Naider, F. (1993). Proline-dependent structural and biological properties of peptides and proteins. Crit. Rev. Biochem. Mol. Biol. 28, 31–81.

Zucker, S., Drews, M., Conner, C., Foda, H. D., DeClerck, Y. A., Langley, K. E., Bahou, W. F., Docherty, A. J., and Cao, J. (1998). Tissue inhibitor of metalloproteinase-2 (TIMP-2) binds to the catalytic domain of the cell surface receptor, membrane type 1-matrix metalloproteinase 1 (MT1-MMP). Journal of Biological Chemistry 273, 1216–1222.

Supplemental References

Fodstad, O., Aamdal, S., McMenamin, M., Nesland, J. M., and Pihl, A. (1988). A new experimental metastasis model in athymic nude mice, the human malignant melanoma LOX. Int. J. Cancer. 41, 442–449.

Haseloff, J. and Gerlach, W. L. Simple RNA enzymes with new and highly specific endoribonuclease activities. Nature 334[18 Aug. 1988], 585–591. 1988.

Kaspari, A., Diefenthal, T., Grosche, G., Schierhom, A., Demuth, and HU (1996). Substrates containing phosphorylated residues adjacent to proline decrease the cleavage by proline-specific peptidases. Biochimica et Biophysica Acta 1293, 147–153.

Kem, F. G., McLeskey, S. W., Zhang, L., Kurebayashi, J., Liu, Y., Ding, I. Y., Kharbanda, S., Chen, D., Miller, D., Cullen, K., and et al (1994). Transfected MCF-7 cells as a model for breast-cancer progression. Breast Cancer Res. Treat. 31, 153–165.

Thompson, E. W., Paik, S., Brunner, N., Sommers, C. L., Zugmaier, G., Clarke, R., Shima, T. B., Torri, J., Donahue, S., Lippman, M. E., Martin, G. R., and Dickson, R. B. (1992). Association of increased basement membrane invasiveness with absence of estrogen receptor and expression of vimentin in human breastcancer cell lines. J. Cell Physiol. 150, 534–544.

Vivier, I., Marguet, D., Naquet, P., Bonicel, J., Black, D., Li, C. X., Bemard,A.M., Gorvel, J. P., and Pierres, M. (1991). Evidence that thymocyte-activating molecule is mouse CD26 (dipeptidyl peptidase IV). J. Immunol. 147, 447–454.

Yan, H.-C., Juhasz,I., Pilewski, J., Murphy, G. F., Herlyn, M., and Albeida, S. M. (1993). Human/severe combined immunodeficient mouse chimeras. J. Clin. Invest. 91, 986–996.

The invention claimed is:

1. A bispecific antibody comprising an antigen binding portion of monoclonal antibody E19 (ATCC PTA-3378) or E26 (ATCC PTA-3377) that specifically binds to an epitope of a mammalian dipeptidyl peptidase IV, and an antigen binding portion of an antibody that specifically binds to a second epitope.

2. A bispecific antibody according to claim 1, wherein the second epitope is an epitope of seprase, an epitope of MT1-MMP, an epitope of MMP-2 or an epitope of $\alpha(3)\beta(1)$-integrin.

3. A composition comprising an effective amount of a bispecific antibody according to claim 1 and a pharmaceutically acceptable carrier.

* * * * *

UNITED STATES PATENT AND TRADEMARK OFFICE
CERTIFICATE OF CORRECTION

PATENT NO. : 7,250,492 B2 Page 1 of 1
APPLICATION NO. : 10/727211
DATED : July 31, 2007
INVENTOR(S) : Wen-Tien Chen It is certified that error appears in the above-identified patent and that said Letters Patent is hereby corrected as shown below:

IN THE SPECIFICATION:

Please add to column 1, after line 20,

--This invention was made with government support under grant number CA039077 awarded by The National Institute of Health. The government has certain rights in the invention.--

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,250,492 B2  Page 1 of 1
APPLICATION NO. : 10/727211
DATED : July 31, 2007
INVENTOR(S) : Wen-Tien Chen It is certified that error appears in the above-identified patent and that said Letters Patent is hereby corrected as shown below:

IN THE SPECIFICATION:

Column 2, line 38,      now reads "artritis"
should read -- arthritis --

Column 18, line 25,      now reads "mim-reservoir"
should read -- mini-reservoir --

Column 23, line 8,      now reads "as an adhesin receptor"
should read -- as an adhesion receptor --

Column 27, line 12,      now reads "seprase+/DPPJV+"
should read -- seprase+/DPPIV+ --

Column 28, line 57,      now reads "Altematively, continuous"
should read -- Alternatively, continuous --

Signed and Sealed this

Ninth Day of February, 2010

David J. Kappos
*Director of the United States Patent and Trademark Office*